(12) United States Patent
Conrad et al.

(10) Patent No.: US 6,716,423 B1
(45) Date of Patent: Apr. 6, 2004

(54) RECOMBINANT NEOSPORA ANTIGENS AND THEIR USES

(75) Inventors: Patricia A. Conrad, Davis, CA (US); Bradd C. Barr, Davis, CA (US); Mark L. Anderson, Davis, CA (US); Karen W. Sverlow, Vacaville, CA (US)

(73) Assignee: The Regents of the University of California, Oakland, CA (US)

( * ) Notice: Subject to any disclaimer, the term of this patent is extended or adjusted under 35 U.S.C. 154(b) by 29 days.

(21) Appl. No.: 09/612,858

(22) Filed: Jul. 10, 2000

Related U.S. Application Data

(63) Continuation of application No. 09/281,766, filed on Mar. 30, 1999, now Pat. No. 6,376,196, which is a continuation-in-part of application No. 08/645,951, filed on May 10, 1996, now Pat. No. 5,889,166, which is a continuation-in-part of application No. 08/327,516, filed on Oct. 20, 1994, now Pat. No. 5,707,617, which is a continuation-in-part of application No. 08/215,858, filed on Mar. 21, 1994, now abandoned.

(51) Int. Cl.$^7$ .................. A61K 39/00; A61K 39/38; A61K 39/02; A01N 63/00; A01N 65/00
(52) U.S. Cl. .................. 424/93.1; 424/93.7; 424/184.1; 424/234.1
(58) Field of Search .................. 424/184.1, 93.1, 424/93.7, 234.1

(56) References Cited

U.S. PATENT DOCUMENTS

| | | |
|---|---|---|
| 4,431,739 A | 2/1984 | Riggs et al. |
| 5,643,718 A * | 7/1997 | Kim et al. |
| 5,707,617 A | 1/1998 | Conrad et al. |

FOREIGN PATENT DOCUMENTS

| | | |
|---|---|---|
| WO | WO 95/25541 | 9/1995 |
| WO | WO 97/39009 | 10/1997 |

OTHER PUBLICATIONS

Anderson, et al. J. Am. Vet Med. Assoc., 198:241–244 (1991).
Barr, et al. J. Vet. Diagn. Invest., 3:39–46 (1991).
Barr, et al. Vet. Pathol., 27:354–361 (1990).
Barr, et al. Vet. Pathol., 28:110–116 (1991).
Barta, et al., Parasitology Research, 78:689–694 (1992).
Baszler, et al., J. of Clin. Micro., 34:1423–1428 (1996).
Bjerkas, et al., Clin. Diag. Lab. Immunol., 1(2):214–221 (1994).
Bjorkman, et al., Parasite Immunology, 16:643–648 (1994).
Conrad, et al., J. Vet. Diagn. Invest., 5:572–578 (1993).
Conrad, Parasitology, 106:239–249 (1993).
Dubey, et al. J. Am. Vet Med. Assoc., 193:1259–1263 (1988).
Dubey, et al., J. Am. Vet Med. Assoc., 201(5):709–713 (1992).
Dubey, et al. J. of Parasitology, 76(5):732–734 (1990).
Dubey, et al. J. Protozool. Res., 2:40–52 (1992).
Lally, et al., Am .J. Trop. Med. Hyg. 53(2):288 (1995).
Lally, et al., Clin. Diag. Lab. Immunol., 3:275–279 (1996).
Lally, et al., Mol. and Biochem. Parasitology., 75:169–178 (1996).
Lindsay, et al., "Neospora–Induced Protozoal Abortions in Cattle", *The Compendium*, 15(6):882–889. 1993.
Lindsay & Dubey, Am. J. Vet. Res., 50:1981–1983 (1989).
Pare, et al., J. Vet. Parasitology, 34:145–148 (1989).
Shivaprasad, et al., Vet. Parasitology, 34:145–148 (1989).
Speer, et al., Infect. and Immun., 50:566–571 (1988).

* cited by examiner

*Primary Examiner*—Mark Navarro
(74) *Attorney, Agent, or Firm*—Townsend and Townsend and Crew L.L.P.

(57) ABSTRACT

The present invention provides isolated bovine Neospora cultures. Also provided are recombinant immunodominant Neospora antigens. The cultures and antigens are used to develop diagnostic assays for the detection of Neospora infections in cattle and other animals. Also provided are pharmaceutical compositions for the treatment and prevention of Neospora infections.

15 Claims, 3 Drawing Sheets

¹INACURATION OF LACHYZOTTE (413, 416) OR UNINFECTED (408) CULTURES.
²FETUSES RECOVERED BY CAESERIAN SECTION (413) OR AT EUTHANASIA (408)

¹CRITERIA FOR DETERMINING INFECTION STATUS IS AS DESCRIBED IN MATERIALS AND METHODS.

²SERA COLLECTED FROM DAM AT TIME OF ABORTION OR CALVING.

FIG. 5A

```
     ....  ....
QHPHPHPPRPNPPEASPPQSSPPEPQRPFSQWPHTPHFFHYHPYPGYNLFYFTYHQSPLPYG
```

```
                 ....              ....
PYGRDPCPCASHPYPADDSPLGSYAPDPSPPQSYPPEPSPSKPSPPEGSSPRVPSPHRHPSR
```

SRLPSAVEPSP

FIG. 5B

```
112  GGAAACAGTGAA---GAGCAGT-ATGTGGAA   138
     ||||| | ||||||   |||||| || ||||
139  GGAACC-GTGAACGGGAGCAGTGATCCGGAA   160
```

Figure 5. a.) Peptide repeats for clone N54 are as follows: SPPQS(S/Y)PPEP (bolded), HP(H/Y)P (underlined and italicized), SPP(E/Q) (*above each amino acid), SY(A/P)P(D/E)PS (broken underline). b.) Extended tandem DNA repeat within clone N57 exhibits divergence from one another.

US 6,716,423 B1

RECOMBINANT NEOSPORA ANTIGENS AND THEIR USES

This application is a continuation of patent application Ser. No. 09/281,766 filed Mar. 30, 1999, now U.S. Pat. No. 6,376,196, which is a Continuation in Part (CIP) of application Ser. No. 08/645,951, filed May 10, 1996 and issued as U.S. Pat. No. 5,889,166 on Mar. 30, 1999, which is a Continuation in Part (CIP) of application Ser. No. 08/327,516, filed Oct. 20, 1994 and issued as U.S. Pat. No. 5,707,617 on Jan. 13, 1998, which is a Continuation in Part (CIP) of application Ser. No. 08/215,858, filed Mar. 21, 1994 (now abandoned). The disclosure of each of these applications is incorporated by reference in its entirety and for all purposes.

BACKGROUND OF THE INVENTION

A distinct pattern of inflammatory lesions, consisting of focal non-suppurative necrotizing encephalitis, non-suppurative myocarditis and myositis have been observed in many aborted bovine fetuses submitted for diagnosis. The pattern of lesions, particularly in the brain, is similar to those seen with *Toxoplasma gondii* infections in sheep. However, cattle have been reported to be resistant to *T. gondii* infection (Dubey, *Vet. Parasit.* 22:177–202 (1986)). In 1988, a cyst-forming protozoal parasite was first identified by histopathological examination in fetuses (Barr, et al., *Vet. Parasit.* 27:354–61 (1990)). This parasite was morphologically similar to Toxoplasma, except that some of the cysts had thick walls, which was more similar to the *Neospora caninum*-like protozoan observed by Thilsted & Dubey (*J. Vet. Diagnos. Invest.* 1:205–9 (1989)) in aborted fetuses from a dairy in New Mexico.

Further studies showed the protozoal parasites associated with inflammatory lesions in aborted fetuses and neonatal calves in California had ultrastructural and antigenic features that were most similar to *N. caninum* parasites which were originally isolated from dogs (Dubey, et al., *JAVAM* 193:1259–63 (1988)). However, differences in the antigenic reactivity of the bovine protozoan and *N. caninum* when tested with a panel of antisera indicated they might not be from the same species (Barr, et al., *Vet. Pathol* 28:110–16 (1991)).

A more complete understanding of the identity and biology of these bovine protozoa requires establishing continuous in vitro cultures of the parasites. Such cultures would also be valuable in the development of diagnostic assays and pharmaceutical compositions for the treatment and prevention of Neospora infections. The present invention addresses these and other needs.

SUMMARY OF THE INVENTION

In order to limit the spread of neosporosis, the development of an improved diagnostic test and a better understanding of the basic biology of the parasite are required. This invention contributes to this understanding by provideing two antigens, N54 and N57, which can be used in a recombinant antigen-based ELISA. When sera from cattle of known disease status were tested (as will be described in more detail below) on the N54-based ELISA, N57-based ELISA, and the tachyzoite lysate-based ELISA, the recombinant antigen-based ELISAs had higher sensitivities and higher or similar specificities compared to the conventional lysate-based ELISA. Thus, the recombinant antigen-based ELISAs can be used for the serodiagnosis of bovine neosporosis.

In addition, this invention provides for NC-p65, which contains the N54 cDNA fragment. The discovery of this full-length cDNA, the encoded protein as well as its function allows the development of vaccines and therapeutics that will help to eliminate this devastating disease of cattle.

Specifically, this invention provides methods of detecting the presence of antibodies specifically immunoreactive with a bovine Neospora antigen in a biological sample (e.g., bovine serum). The method comprises contacting the sample with the Neospora antigen, thereby forming an antigen/antibody complex, and detecting the presence or absence of the complex. The Neospora antigen is typically an isolated recombinantly produced immunodominant Neospora antigen. In some embodiments, the antigen is immobilized on a solid surface and the complex is detected using a fluorescently labeled anti-bovine antibody.

The invention further provides methods of detecting the presence of Neospora in a biological sample. These methods comprise contacting the sample with an antibody specifically immunoreactive with a Neospora antigen, thereby forming an antigen/antibody complex, and detecting the presence or absence of the complex. The antibody (e.g., a monoclonal antibody) may be immobilized on a solid surface and the complex detected using a second labeled antibody. Typically, the biological sample is bovine fetal neurological tissue.

The methods of the invention also include detecting the presence of Neospora-specific nucleic acids in a biological sample by contacting the sample with an oligonucleotide probe which specifically hybridizes with a target Neospora-specific polynucleotide sequence and detecting the presence or absence of hybridization complexes. The methods may further comprise amplifying the target Neospora-specific polynucleotide sequence.

The invention further provides for pharmaceutical compositions comprising a pharmaceutically acceptable carrier and an immunogenically effective amount of a bovine Neospora antigen, such as a recombinantly produced bovine Neospora polypeptide.

The pharmaceutical compositions are used in protecting a bovine animal from infection by bovine Neospora. The compositions are preferably administered to a cow or heifer when the animal is breeding. The pharmaceutical composition is usually administered parenterally.

BRIEF DESCRIPTION OF THE DRAWINGS

FIGS. 5A and 5B show sequence motifs in two immunodominant cDNA clones isolated from Neospora.

DESCRIPTION OF THE PREFERRED EMBODIMENTS

Definitions

Figure 1:
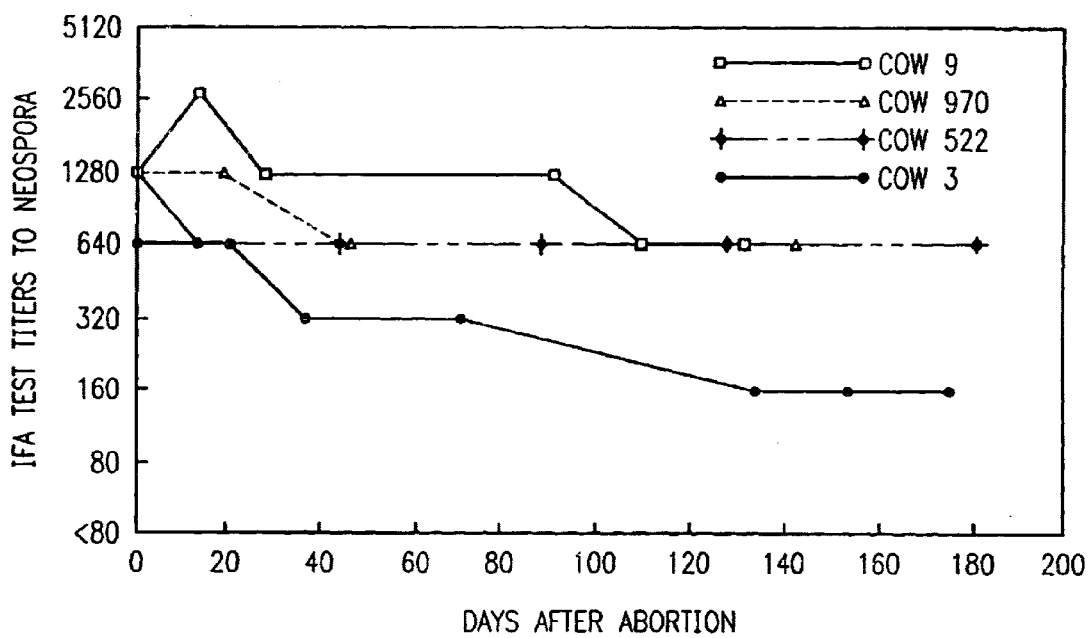
FIG. 1 shows indirect fluorescent antibody (IFA) titers of serial samples from four cows that aborted Neospora-infected fetuses.

"Antibody" refers to an immunoglobulin molecule able to bind to a specific epitope on an antigen. Antibodies can be a polyclonal mixture or monoclonal. Antibodies can be intact immunoglobulins derived from natural sources or from recombinant sources and can be immunoreactive portions of intact immunoglobulins. Antibodies may exist in a variety of forms including, for example, Fv, Fab, and F(ab)$_2$, as well as in single chains. Single-chain antibodies, in which genes for a heavy chain and a light chain are combined into a single coding sequence, may also be used.

"Biological sample" refers to any sample obtained from a living or dead organism. Examples of biological samples include biological fluids and tissue specimens. Examples of tissue specimens include fetal brain tissue, spinal cord, and placenta. Examples of biological fluids include blood, serum, plasma, urine, ascites fluid, cerebrospinal fluid and fetal fluid.

A "biologically pure bovine Neospora culture" refers to a continuous in vitro culture of bovine Neospora organisms (e.g. tachyzoites) which is substantially free of other organisms other than the host cells in which Neospora tachyzoites are grown. A culture is substantially free of other organisms if standard harvesting procedures (as described below) result in a preparation which comprises at least about 95%, preferably 99% or more of the organism, e.g., Neospora tachyzoites.

"Bovine Neospora" refers to Neospora or "Neospora-like" protozoans identified in or isolated from bovine tissues and fluids. Typically, the protozoal parasites can be isolated from neurological tissue of aborted bovine fetuses or congenitally infected calves. Exemplary isolates have been deposited with the American Type Culture Collection, as described below.

A bovine Neospora "protein" or "polypeptide" includes allelic variations normally found in the natural population and changes introduced by recombinant techniques. Those of skill recognize that proteins can be modified in a variety of ways including the addition, deletion and substitution of amino acids.

A "recombinantly produced immunodominant Neospora antigen" is a recombinantly produced polypeptide comprising one or more immunodominant epitopes. Exemplary recombinant antigens of the invention include SEQ ID NOs. 10, 12, 14 and 19. Such antigens are encoded by SEQ ID NOs. 9, 11, 13 and 18. Terms used to describe the recombinant antigens and the nucleic acids which encode them will be understood by those of skill in the art to include sequences which are substantially identical to the exemplified sequences. Substantial identity can be determined as described below.

"Nucleic acids" and "polynucleotides", as used herein, may be DNA or RNA. One of skill will recognize that for use in the expression of Neospora proteins or as diagnostic probes, polynucleotide sequences need not be identical and may be substantially identical to sequences disclosed here. In particular, where the inserted polynucleotide sequence is transcribed and translated to produce a functional polypeptide, one of skill will recognize that because of codon degeneracy a number of polynucleotide sequences will encode the same polypeptide.

The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence, as measured using one of the following sequence comparison algorithms or by visual inspection.

The phrase "substantially identical," in the context of two nucleic acids or polypeptides, refers to two or more sequences or subsequences that have at least 60%, preferably 80%, most preferably 90–95% nucleotide or amino acid residue identity, when compared and aligned for maximum correspondence, as measured using one of the following sequence comparison algorithms or by visual inspection.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel,et al., supra).

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, *J. Mol. Evol.* 35:351–360 (1987). The method used is similar to the method described by Higgins & Sharp, *CABIOS* 5:151–153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps.

Another example of algorithm that is suitable for determining percent sequence identity and sequence similarity is the BLAST algorithm, which is described in Altschul et al., *J. Mol. Biol.* 215:403–410 (1990). Software for performing BLAST analyses is publicly available through the National Center for Biotechnology Information (http://www.ncbi.nlm.nih.gov/). This algorithm involves first identifying high scoring sequence pairs (HSPS) by identifying short words of length W in the query sequence, which either match or satisfy some positive-valued threshold score T when aligned with a word of the same length in a database sequence. T is referred to as the neighborhood word score threshold (Altschul el al, supra.). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. For identifying whether a nucleic acid or polypeptide is within the scope of the invention, the default parameters of the BLAST programs are suitable. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89:10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873–5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A further indication that two nucleic acid sequences or polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions, as described below.

The phrase "selectively hybridizes to" refers to the binding, duplexing, or hybridizing of a molecule only to a particular nucleotide sequence under stringent hybridization conditions when that sequence is present in a complex mixture (e.g., total cellular) DNA or RNA. The phrase "stringent hybridization conditions" refers to conditions under which a probe will hybridize to its target subsequence, but to no other sequences. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993). Generally, stringent conditions are selected to be about 5–10° C. lower than the thermal melting point (Tm) for the specific sequence at a defined ionic strength pH. The Tm is the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0 sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents as formamide.

An example of highly stringent wash conditions is 0.1 5M NaCl at from 70 to 80° C. with 72° C. being preferable for about 15 minutes. An example of stringent wash conditions is a 0.2×SSC wash at about 60 to 70° C., preferably 65° C. for 15 minutes (see, Sambrook, supra for a description of SSC buffer). Often, a high stringency wash is preceded by a low stringency wash to remove background probe signal. An example medium stringency wash for a duplex of, e.g., more than 100 nucleotides, is 1×SSC at 40 to 50° C., preferably 45° C. for 15 minutes. An example low stringency wash for a duplex of, e.g., more than 100 nucleotides, is 4–6×SSC at 35 to 45° C., with 40° C. being preferable, for 15 minutes. In general, a signal to noise ratio of 2×(or higher) than that observed for an unrelated probe in the particular hybridization assay indicates detection of a specific hybridization.

The phrase "specifically immunoreactive with", when referring to a protein or peptide, refers to a binding reaction between the protein and an antibody which is determinative of the presence of the protein in the presence of a heterogeneous population of proteins and other compounds. Thus, under designated immunoassay conditions, the specified antibodies bind to a particular protein and do not bind in a significant amount to other proteins present in the sample. Specific binding to an antibody under such conditions may require an antibody that is selected for its specificity for a particular protein. A variety of immunoassay formats may be used to select antibodies specifically immunoreactive with a particular protein and are described in detail below.

The phrase "substantially pure" or "isolated" when referring to a Neospora peptide or protein, means a chemical composition which is free of other subcellular components of the Neospora organism. Typically, a monomeric protein is substantially pure when at least about 85% or more of a sample exhibits a single polypeptide backbone. Minor variants or chemical modifications may typically share the same polypeptide sequence. Depending on the purification procedure, purities of 85%, and preferably over 95% pure are possible. Protein purity or homogeneity may be indicated by a number of means well known in the art, such as polyacrylamide gel electrophoresis of a protein sample, followed by visualizing a single polypeptide band on a polyacrylamide gel upon silver staining. For certain purposes high resolution will be needed and HPLC or a similar means for purification utilized.

Introduction

Neospora tachyzoite cultures of the invention have been deposited with the American Type Culture Collection, Rockville, Md. on Mar. 17, 1994 and given Accession Numbers 75710 (BPA1) and 75711 (BPA6).

These isolates were obtained from tissue homogenates of brain and/or spinal cord of an aborted bovine fetus and congenitally infected calves. Immunohistochemistry was used to identify the tachyzoite and/or cysts associated with lesions in the tissues of these fetuses and calves as Neospora parasites prior to isolation. Tachyzoite stages of the isolates were grown in stationary monolayer cultures of bovine fetal trophoblasts, aortic endothelial cells and/or macrophages. Electron microscopic studies were used to characterize the ultrastructural features of the BPA1 isolate. Antigenically, tachyzoites of 5 separate isolates react strongly with antisera to Neospora and show little or no reactivity with antisera to *Toxoplasma gondii* or *Hammondia hammondi*. Based on these ultrastructural and antigenic characteristics, these parasites can be distinguished from the most closely related and morphologically similar genera of protozoa, Toxoplasma, Hammondia and Sarcocystis.

In addition, partial sequences (500–550 base pairs) of the 5' end of the nuclear small subunit (nss)-rRNA gene for three of the bovine Neospora isolates (BPA1, BPA3 and BPA5) have been obtained and shown to be identical. The more complete 1.8 kilobase sequence of the nss-rRNA gene of the BPA1 isolate was obtained and compared to the sequences for this gene in other coccidial parasites. Alignment of these sequences with published sequences of *Neospora caninum, Cryptosporidium parvum, Sarcocystis muris* and *Toxoplasma gondii* showed that the bovine Neospora isolate is genotypically unique.

As explained in detail below, the isolates are used to develop a variety of diagnostic assays as well as pharmaceutical compositions for treatment and prevention of infection.

Preparation of Neospora Polypeptides and Nucleic Acids

Standard protein purification techniques can be used to isolate proteins from the tachyzoites or bradyzoites derived from the cultures provided here. Such techniques include selective precipitation with such substances as ammonium sulfate, column chromatography, immunopurification methods, and the like. See, for instance, R. Scopes, Protein Purification: Principles and Practice, Springer-Verlag: New York (1982).

Using standard immunoblot techniques 11 proteins with molecular weights of approximately 106, 49.5, 48, 33, 32.5, 30, 28, 26, 19, 18 and 17 kilodaltons (kd) have been identified. All of these proteins are specifically recognized by antibodies from Neospora infected cattle. Standard protein purification methods can be used to purify these proteins and produce polyclonal or monoclonal antibodies for use in the diagnostic methods described below. Two of these antigens (approximately 106 and 19 kd) have been shown to be useful in enzyme-linked immunoassays (ELISA) for the detection of Neospora-specific antibodies in infected cattle.

Rather than extract the proteins directly from cultured tachyzoites, one of skill will recognize that nucleic acids derived from the cultures can be used for recombinant expression of immunodominant antigens of the invention both presently known and unknown. In these methods, e.g., cDNA libraries are created from cultured tachyzoites. The libraries are screened for immunodominant antigens, either through, for example, selective hybridization to nucleic acids which encode known immunodominant antigens or by expression screening. In expression screening, the cDNA libraries are screened for the presence of immunodominant antigens using antibodies raised against the tachyzoite of interest. By using these methods, immunodominant antigens from different cultures or species of Neospora can be identified.

After candidate cDNA is identified, the nucleic acids encoding the proteins of interest are introduced into suitable host cells, followed by induction of the cells to produce large amounts of the protein. The isolation of two exemplary nucleic acids is described in Example 6, below. The invention relies on routine techniques in the field of recombinant genetics, well known to those of ordinary skill in the art. A basic text disclosing the general methods of use in this invention is Sambrook et al., *Molecular Cloning, A Laboratory Manual*, Cold Spring Harbor Publish., Cold Spring Harbor, N.Y. 2nd ed. (1989).

Nucleic acids for use as diagnostic oligonucleotide probes or for the recombinant expression of proteins can be isolated using a number of techniques. For instance, portions of proteins isolated from the cultures discussed above can be sequenced and used to design degenerate oligonucleotide probes to screen a cDNA library. Amino acid sequencing is performed and oligonucleotide probes are synthesized according to standard techniques as described, for instance, in Sambrook et al., supra. Alternatively, oligonucleotide probes useful for identification of desired genes can also be prepared from conserved regions of related genes in other species.

Alternatively, polymerase chain reaction technology (PCR) can be used to amplify nucleic acid sequences of the desired gene directly from mRNA, from cDNA, from genomic libraries or cDNA libraries. Polymerase chain reaction (PCR) or other in vitro amplification methods may also be useful, for example, to clone nucleic acid sequences that code for proteins to be expressed, to make nucleic acids to use as probes for detecting the presence of the mRNA in physiological samples, for nucleic acid sequencing, or for other purposes. For a general overview of PCR see *PCR Protocols: A Guide to Methods and Applications.* (Innis, M, Gelfand, D., Sninsky, J. and White, T., eds.), Academic Press, San Diego (1990).

Standard transfection methods are used to produce prokaryotic, mammalian, yeast or insect cell lines which express large quantities of the desired polypeptide, which is then purified using standard techniques. See, e.g., Colley et al., *J. Biol. Chem.* 264:17619–17622, 1989; and Guide to Protein Purification, supra.

The nucleotide sequences used to transfect the host cells can be modified to yield Neospora polypeptides with a variety of desired properties. For example, preferred codons can be used to aid in the expression of polypeptides by specific cells. In addition, the polypeptides can vary from the naturally-occurring sequence at the primary structure level by amino acid, insertions, substitutions, deletions, and the like. These modifications can be used in a number of combinations to produce the final modified protein chain.

The amino acid sequence variants can be prepared with various objectives in mind, including facilitating purification and preparation of the recombinant polypeptide. The modified polypeptides are also useful for modifying plasma half life, improving therapeutic efficacy, and lessening the severity or occurrence of side effects during therapeutic use. The amino acid sequence variants are usually predetermined variants not found in nature but exhibit the same immunogenic activity as naturally occurring protein. In general, modifications of the sequences encoding the polypeptides may be readily accomplished by a variety of well-known techniques, such as site-directed mutagenesis (see, Gillman & Smith, *Gene* 8:81–97, 1979) and Roberts, el al., *Nature* 328:731–734, 1987).

Examples of modifications that may be achieved by one of skill include preparation of amino acid and polypeptide variants with increased affinity for a particular receptor molecule; preparation of polypeptide variants with increased cross-reactivity among different T-cells; or by production of a subdominant antigen (e.g., by substitution of residues which increase affinity but are not present on the immunodominant antigen).

Polypeptides having a desired activity may be modified as necessary (e.g., having variants created thereof) to provide certain desired attributes, e.g., improved pharmacological characteristics, while increasing or at least retaining substantially all of the biological activity of the unmodified polypeptide and, e.g., to activate the desired T cell. Moreover, polypeptides which lack a desired activity can be modified so as to thereby have that activity.

The polypeptides can also be modified by extending or decreasing the compound's amino acid sequence, e.g., by the addition or deletion of amino acids. Polypeptides of the invention can also be modified by altering the order or composition of certain residues, it being readily appreciated that certain amino acid residues essential for biological activity, e.g., those at critical contact sites and conserved residues, may generally not be altered without an adverse effect on a biological activity. In certain contexts, however, it may be desirable to produce peptides which lead to an "adversely affected" biological activity.

Most modifications are evaluated by routine screening in a suitable assay for the desired characteristic. For instance, the effect of various modifications on the ability of the polypeptide to elicit a protective immune response can be easily determined using in vitro assays. For instance, the polypeptides can be tested for their ability to induce lymphoproliferation, T cell cytotoxicity, or cytokine production using standard techniques.

Modified polypeptides that have various amino acid mimetics or unnatural amino acids are particularly useful, as they tend to manifest increased stability in vivo. More specifically, non-critical amino acids need not be limited to those naturally occurring in proteins, such as L-a-amino acids, or their D-isomers, but may include nonnatural amino acids as well, such as amino acids mimetics, e.g. D- or L-naphylalanine; D- or L- phenylglycine; D- or L-2-thieneylalanine; D- or L-1, -2, 3-, or 4- pyreneylalanine; D- or L-3 thieneylalanine; D- or L-(2-pyridinyl)-alanine; D- or L-(3-pyridinyl)-alanine; D- or L-(2-pyrazinyl)-alanine; D- or L-(4-isopropyl)-phenylglycine; D-(trifluoromethyl)-phenylglycine; D-(trifluoromethyl)-phenylalanine; D-$\rho$-fluorophenylalanine; D- or L-$\rho$-biphenylphenylalanine; D- or L-$\rho$-methoxybiphenylphenylalanine; D- or L-2-indole (alkyl)alanines; and, D- or L-alkylalanines, where the alkyl group can be a substituted or unsubstituted methyl, ethyl, propyl, hexyl, butyl, pentyl, isopropyl, iso-butyl, sec-isotyl, iso-pentyl, or a non-acidic amino acids. Aromatic rings of a nonnatural amino acid include, e.g., thiazolyl, thiophenyl, pyrazolyl, benzimidazolyl, naphthyl, furanyl, pyrrolyl, and pyridyl aromatic rings.

Peptide stability can be assayed in a number of ways. For instance, peptidases and various biological media, such as plasma and serum, have been used to test stability. See, e.g., Verhoef, et al., *Eur. J. Drug Metab. Pharmacokinetics* 11:291 (1986). Half life of the peptides of the present invention is conveniently determined using a 25% serum (v/v) assay. The protocol is generally as follows: Serum, typically bovine, is dilipidated by centrifugation before use. The serum is then diluted to 25% with RPMI-1640 or another suitable tissue culture medium. At predetermined time intervals, a small amount of reaction solution is removed and added to either 6% aqueous trichloroacetic acid (TCA) or ethanol. The cloudy reaction sample is cooled (4° C.) for 15 minutes and then spun to pellet the precipitated serum proteins. The presence of the polypeptides is then determined by reversed-phase HPLC using stability-specific chromatography conditions.

The particular procedure used to introduce the genetic material into the host cell for expression of the polypeptide is not particularly critical. Any of the well known procedures for introducing foreign nucleotide sequences into host cells may be used. These include the use of calcium phosphate transfection, spheroplasts, electroporation, liposomes, microinjection, plasmid vectors, viral vectors and any of the other well known methods for introducing cloned genomic DNA, cDNA, synthetic DNA or other foreign genetic material into a host cell (see Sambrook et al., supra). It is only necessary that the particular procedure utilized be capable of successfully introducing at least one gene into the host cell which is capable of expressing the gene.

Any of a number of well known cells and cell lines can be used to express the polypeptides of the invention. For instance, prokaryotic cells such as *E. coli* can be used. Eukaryotic cells include, yeast, Chinese hamster ovary (CHO) cells, COS cells, and insect cells.

The particular vector used to transport the genetic information into the cell is also not particularly critical. Any of the conventional vectors used for expression of recombinant proteins in prokaryotic and eukaryotic cells may be used. Expression vectors for mammalian cells typically contain regulatory elements from eukaryotic viruses.

The expression vector typically contains a transcription unit or expression cassette that contains all the elements required for the expression of the polypeptide DNA in the host cells. A typical expression cassette contains a promoter operably linked to the DNA sequence encoding a polypeptide and signals required for efficient polyadenylation of the transcript. The term "operably linked" as used herein refers to linkage of a promoter upstream from a DNA sequence such that the promoter mediates transcription of the DNA sequence. The promoter is preferably positioned about the same distance from the heterologous transcription start site as it is from the transcription start site in its natural setting. As is known in the art, however, some variation in this distance can be accommodated without loss of promoter function.

Following the growth of the recombinant cells and expression of the polypeptide, the culture medium is harvested for purification of the secreted protein. The media are typically clarified by centrifugation or filtration to remove cells and cell debris and the proteins are concentrated by adsorption to any suitable resin or by use of ammonium sulfate fractionation, polyethylene glycol precipitation, or by ultrafiltration. Other routine means known in the art may be equally suitable. Further purification of the polypeptide can be accomplished by standard techniques, for example, affinity chromatography, ion exchange chromatography, sizing chromatography, His$_6$ tagging and Ni-agarose chromatography (as described in Dobeli, er al., *Mol. and Biochem. Parasit.* 41:259–268 (1990)), or other protein purification techniques to obtain homogeneity. The purified proteins are then used to produce pharmaceutical compositions, as described below.

An alternative method of preparing recombinant polypeptides useful as vaccines involves the use of recombinant viruses (e.g., vaccinia). Vaccinia virus is grown in suitable cultured mammalian cells such as the HeLa S3 spinner cells, as described by Mackett, Smith and Moss, "*The construction and characterization of Vaccinia Virus Recombinants Expressing Foreign Genes*" in "*DNA cloning Vol. II. A practical approach*", Ed. D. M. Glover, IRL Press, Oxford, pp 191–211.

Antibody Production

The isolated proteins or cultures of the present invention can be used to produce antibodies specifically reactive with Neospora antigens. If isolated proteins are used, they may be recombinantly produced or isolated from Neospora cultures. Synthetic peptides made using the protein sequences may also be used.

Methods of production of polyclonal antibodies are known to those of skill in the art. In brief, an immunogen, preferably a purified protein, is mixed with an adjuvant and animals are immunized. When appropriately high titers of antibody to the immunogen are obtained, blood is collected from the animal and antisera is prepared. Further fractionation of the antisera to enrich for antibodies reactive to Neospora proteins can be done if desired. (See Harlow and Lane, *Antibodies: A Laboratory Manual*, Cold Spring Harbor Pubs., N.Y. (1988)).

Polyclonal antisera to the BPA1 and BPA3 isolates have been produced and evaluated. The polyclonal antisera are used to identify and characterize Neospora tachyzoite and bradyzoite stages in the tissues of infected animals using, for instance, immunoperoxidase test procedures described in Anderson et al. *JAVMA* 198:241 (1991) and Barr et al. *Vet. Pathol.* 28:110–116(1991).

Monoclonal antibodies may be obtained by various techniques familiar to those skilled in the art. Briefly, spleen cells from an animal immunized with a desired antigen are immortalized, commonly by fusion with a myeloma cell (See, Kohler and Milstein, *Eur. J. Immunol.* 6:511–519 (1976)). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host.

For instance, the BPA1 isolate has been used to immunize mice to obtain sensitized B cells for hybridoma production. Using these cells, monoclonal antibodies to the 48 kd and 70 kd Neospora proteins have been obtained. The monoclonal antibodies produced are used, for instance, in ELISA diagnostic tests, immunohistochemical tests, for the in vitro evaluation of parasite invasion, to select candidate antigens for vaccine development, protein isolation, and for screening genomic and cDNA libraries to select appropriate gene sequences.

Diagnosis of Neospora Infections

The present invention also provides methods for detecting the presence or absence of Neospora in a biological sample. For instance, antibodies specifically reactive with Neospora can be detected using either proteins or the isolates described here. The proteins and isolates can also be used to raise specific antibodies (either monoclonal or polyclonal) to detect the antigen in a sample. In addition, the nucleic acids disclosed and claimed here can be used to detect Neospora-specific sequences using standard hybridization techniques. Each of these assays is described below.

A. Immunoassays

For a review of immunological and immunoassay procedures in general, see *Basic and Clinical Immunology* 7th Edition (D. Stites and A. Terr ed.) 1991. The immunoassays of the present invention can be performed in any of several configurations, which are reviewed extensively in *Enzyme Immunoassay*, E. T. Maggio, ed., CRC Press, Boca Raton, Fla. (1980); "Practice and Theory of Enzyme Immunoassays," P. Tijssen, *Laboratory Techniques in Biochemistry and Molecular Biology*, Elsevier Science Publishers B.V. Amsterdam (1985). For instance, the proteins and antibodies disclosed here are conveniently used in ELISA, immunoblot analysis and agglutination assays. Particularly preferred assay formats include the indirect fluorescent antibody assay as described in Example 2.

In brief, immunoassays to measure anti-Neospora antibodies or antigens can be either competitive or noncompetitive binding assays. In competitive binding assays, the sample analyte (e.g., anti-Neospora antibodies) competes with a labeled analyte (e.g., anti-Neospora monoclonal antibody) for specific binding sites on a capture agent (e.g., isolated Neospora protein) bound to a solid surface. The concentration of labeled analyte bound to the capture agent is inversely proportional to the amount of free analyte present in the sample.

Noncompetitive assays are typically sandwich assays, in which the sample analyte is bound between two analyte-specific binding reagents. One of the binding agents is used as a capture agent and is bound to a solid surface. The second binding agent is labeled and is used to measure or detect the resultant complex by visual or instrument means.

A number of combinations of capture agent and labeled binding agent can be used. For instance, an isolated Neospora protein or culture can be used as the capture agent and labeled anti-bovine antibodies specific for the constant region of bovine antibodies can be used as the labeled binding agent. Goat, sheep and other non-bovine antibodies specific for bovine immunoglobulin constant regions (e.g., γ or μ) are well known in the art. Alternatively, the anti-bovine antibodies can be the capture agent and the antigen can be labeled.

Various components of the assay, including the antigen, anti-Neospora antibody, or anti-bovine antibody, may be bound to a solid surface. Many methods for immobilizing biomolecules to a variety of solid surfaces are known in the art. For instance, the solid surface may be a membrane (e.g., nitrocellulose), a microtiter dish (e.g., PVC or polystyrene) or a bead. The desired component may be covalently bound or noncovalently attached through nonspecific bonding.

Alternatively, the immunoassay may be carried out in liquid phase and a variety of separation methods may be employed to separate the bound labeled component from the unbound labeled components. These methods are known to those of skill in the art and include immunoprecipitation, column chromatography, adsorption, addition of magnetizable particles coated with a binding agent and other similar procedures.

An immunoassay may also be carried out in liquid phase without a separation procedure. Various homogeneous immunoassay methods are now being applied to immunoassays for protein analytes. In these methods, the binding of the binding agent to the analyte causes a change in the signal emitted by the label, so that binding may be measured without separating the bound from the unbound labeled component.

Western blot (immunoblot) analysis can also be used to detect the presence of antibodies to Neospora in the sample.

This technique is a reliable method for confirming the presence of antibodies against a particular protein in the sample. The technique generally comprises separating proteins by gel electrophoresis on the basis of molecular weight, transferring the separated proteins to a suitable solid support, (such as a nitrocellulose filter, a nylon filter, or derivatized nylon filter), and incubating the sample with the separated proteins. This causes specific target antibodies present in the sample to bind their respective proteins. Target antibodies are then detected using labeled anti-bovine antibodies.

The immunoassay formats described above employ labeled assay components. The label can be in a variety of forms. The label may be coupled directly or indirectly to the desired component of the assay according to methods well known in the art. A wide variety of labels may be used. The component may be labeled by any one of several methods. Traditionally a radioactive label incorporating $^3H$, $^{125}I$, $^{35}S$, $^{14}C$, or $^{32}P$ was used. Non-radioactive labels include ligands which bind to labeled antibodies, fluorophores, chemiluminescent agents, enzymes, and antibodies which can serve as specific binding pair members for a labeled ligand. The choice of label depends on sensitivity required, ease of conjugation with the compound, stability requirements, and available instrumentation.

Enzymes of interest as labels will primarily be hydrolases, particularly phosphatases, esterases and glycosidases, or oxidoreductases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems which may be used, see U.S. Pat. No. 4,391,904, which is incorporated herein by reference.

Non-radioactive labels are often attached by indirect means. Generally, a ligand molecule (e.g., biotin) is covalently bound to the molecule. The ligand then binds to an anti-ligand (e.g., streptavidin) molecule which is either inherently detectable or covalently bound to a signal system, such as a detectable enzyme, a fluorescent compound, or a chemiluminescent compound. A number of ligands and anti-ligands can be used. Where a ligand has a natural anti-ligand, for example, biotin, thyroxine, and cortisol, it can be used in conjunction with the labelled, naturally occurring anti-ligands. Alternatively, any haptenic or antigenic compound can be used in combination with an antibody.

Some assay formats do not require the use of labeled components. For instance, agglutination assays can be used to detect the presence of the target antibodies. In this case, antigen-coated particles are agglutinated by samples comprising the target antibodies. In this format, none of the components need to be labeled and the presence of the target antibody is detected by simple visual inspection.

B. Detection of Neospora Nucleic Acids

As noted above, this invention also embraces methods for detecting the presence of Neospora DNA or RNA in biological samples. These sequences can be used to detect all stages of the Neospora life cycle (e.g., tachyzoites, bradyzoites, and oocysts) in biological samples from both the bovine host and the definitive host. A variety of methods of specific DNA and RNA measurement using nucleic acid hybridization techniques are known to those of skill in the art. See Sambrook et al., supra.

One method for determining the presence or absence of Neospora DNA in a sample involves a Southern transfer. Briefly, the digested DNA is run on agarose slab gels in buffer and transferred to membranes. In a similar manner, a Northern transfer may be used for the detection of Neospora mRNA in samples of RNA. Hybridization is carried out using labeled oligonucleotide probes which specifically hybridize to Neospora nucleic acids. Labels used for this purpose are generally as described for immunoassays. Visualization of the hybridized portions allows the qualitative determination of the presence or absence of Neospora genes.

A variety of other nucleic acid hybridization formats are known to those skilled in the art. For example, common formats include sandwich assays and competition or displacement assays. Hybridization techniques are generally described in "Nucleic Acid Hybridization, A Practical Approach," Ed. Hades, B. D. and Higgins, S. J., IRL Press, 1985; Gall & Pardue, *Proc. Natl. Acad. Sci.*, U.S.A., 63:378–383 (1969); and John, et al., *Nature*, 223:582–587 (1969).

Sandwich assays are commercially useful hybridization assays for detecting or isolating nucleic acid sequences. Such assays utilize a "capture" nucleic acid covalently immobilized to a solid support and a labeled "signal" nucleic acid in solution.

The biological sample will provide the target nucleic acid. The "capture" nucleic acid and "signal" nucleic acid probe hybridize with the target nucleic acid to form a "sandwich" hybridization complex. To be effective, the signal nucleic acid cannot hybridize with the capture nucleic acid.

The sensitivity of hybridization assays may be enhanced through use of a nucleic acid amplification system which multiplies the target nucleic acid being detected. Examples of such systems include the polymerase chain reaction (PCR) system and the ligase chain reaction (LCR) system. Other methods recently described in the art are the nucleic acid sequence based amplification (NASBA™, Cangene, Mississauga, Ontario) and Q Beta Replicase systems.

An alternative means for detecting Neospora nucleic acids is in situ hybridization. In situ hybridization assays are well known and are generally described in Angerer, et al., *Methods Enzymol.*, 152:649–660 (1987). In situ hybridization assays use cells or tissue fixed to a solid support, typically a glass slide. If DNA is to be probed, the cells are denatured with heat or alkali. The cells are then contacted with a hybridization solution at a moderate temperature to permit annealing of labeled Neospora specific probes. The probes are preferably labeled with radioisotopes or fluorescent reporters.

Exemplary nucleic acid sequences for use in the assays described above include sequences from the nss-rRNA sequences disclosed here. For instance, the primer and probe sequences disclosed in Example 4 can be used to amplify and identify nucleic acids of bovine Neospora in blood, cerebrospinal fluid and fetal fluids, as well as in frozen or formalin-fixed tissue. These primers are particularly useful for the diagnosis of neosporosis and identification of the source of Neospora parasite stages (tachyzoites, bradyzoites and oocysts) in various animal hosts.

Pharmaceutical Compositions Comprising Neospora

The present invention provides biologically pure cultures of bovine Neospora. Two such cultures have been deposited with the ATCC and given ATCC Accession No. 75710 (BPA1), and ATCC Accession No. 75711 (BPA6).

A pharmaceutical composition prepared using anti-Neospora monoclonal antibodies or fragments thereof as well as Neospora proteins or their immunogenic equivalents can be used in a variety of pharmaceutical preparations for the treatment and/or prevention of Neospora infections.

The pharmaceutical compositions are typically used to vaccinate cattle, sheep, goats and other animals infected by Neospora. The compositions of the invention can also be used to treat the definitive host to prevent the shedding of oocysts and subsequent transfer to cattle. The compositions for administration to either cattle or the definitive host can comprise tachyzoite and/or bradyzoite antigens.

An attenuated Neospora vaccine can only be used in the absence of a risk of human infection should the milk or tissues of immunized animals be consumed. Thus, preferred vaccines are subunit vaccines that elicit antibody and cell-mediated immunity (CMI) to antigens of bovine Neospora. Experimental evidence indicates that CMI is an important component of the protective immune response in cattle. A variety of methods for evaluating the specificity of the helper and cytotoxic T cell response to selected antigens in vitro can be used. In addition, as demonstrated below, cows infected using culture-derived tachyzoites mount a protective immune response and prevent transplacental infection of the fetus.

The vaccines of the invention are typically administered orally or parenterally, usually intramuscularly or subcutaneously. For parenteral administration, the antigen may be combined with a suitable carrier. For example, it may be administered in water, saline or buffered vehicles with or without various adjuvants or immunomodulating agents such as aluminum hydroxide, aluminum phosphate, aluminum potassium sulfate (alum), beryllium sulfate, silica, kaolin, carbon, water-in-oil emulsions, oil-in-water emulsions, muramyl dipeptide, bacterial endotoxin, lipid, *Bordetella perlussis*, and the like. Such adjuvants are available commercially from various sources, for example, Merck Adjuvant 6 (Merck and Company, Inc., Rahway, N.J.). Other suitable adjuvants are MPL+TDM Emulsion (RIBBI Immunochem Research Inc. U.S.A.). Other immuno-stimulants include interleukin 1, interleukin 2 and interferon-gamma. These proteins can be provided with the vaccine or their corresponding genetic sequence provided as a functional operon with a recombinant vaccine system such as vaccinia virus. The proportion of antigen and adjuvant can be varied over a broad range so long as both are present in effective amounts.

Vaccine compositions of the invention are administered to a cattle, sheep, or goats susceptible to or otherwise at risk of infection to elicit an immune response against the antigen and thus enhance the animal's own immune response capabilities. Such an amount is defined to be an "immunogenically effective amount." In this use, the precise amounts depend on the judgement of the prescribing veterinarian and would include consideration of the animal's state of health and weight, the mode of administration, the nature of the formulation, and the like. Generally, on a per-dose basis, the concentration of the Neospora antigen can range from about 1 μg to about 100 mg per bovine host. For administration to cattle, a preferable range is from about 100 μg to about 1 mg per unit dose. A suitable dose size is about 1–10 mL, preferably about 1.0 mL. Accordingly, a typical dose for subcutaneous injection, for example, would comprise 1 to 2 mL containing 0.1 to 10 mg of antigen.

A variety of vaccination regimens may be effective in immunizing cattle and other animals. Preferably, female cattle (heifers and cows) are vaccinated just prior to or at the time of breeding so as to prevent abortion and reduce the possibility of congenital infections. A second immunization will be given 2–4 weeks after initial immunization. Calves and adult males may also be vaccinated, if desired. Animals that have been previously exposed to Neospora or have received colostral antibodies from the mother may require booster injections. The booster injection is preferably timed to coincide with times of maximal challenge and/or risk of abortion. Different immunization regimes may be adopted depending on the judgement of the veterinarian.

Vaccines of the invention may comprise a crude extract of Neospora tachyzoites, bradyzoites or other stages. Chemically fixed parasites or cells can also be used. As noted above, preferred vaccines comprise partially or completely purified Neospora protein preparations. The antigen produced by recombinant DNA technology is preferred because it is more economical than the other sources and is more readily purified in large quantities.

In addition to use in recombinant expression systems, the isolated Neospora gene sequences can also be used to transform viruses that transfect host cells in animals. Live attenuated viruses, such as vaccinia or adenovirus, are convenient alternatives for vaccines because they are inexpensive to produce and are easily transported and administered.

Suitable viruses for use in the present invention include, but are not limited to, pox viruses, such as capripox and cowpox viruses, and vaccinia viruses, alpha viruses, adenoviruses, and other animal viruses. The recombinant viruses can be produced by methods well known in the art, for example, using homologous recombination or ligating two plasmids. A recombinant canarypox or cowpox virus can be made, for example, by inserting the DNA's encoding the Neospora protein or fragments thereof into plasmids so that they are flanked by viral sequences on both sides. The DNA's encoding Neospora polypeptides are then inserted into the virus genome through homologous recombination.

Preferentially, a viral vaccine using recombinant vaccinia virus is used. A vaccine prepared utilizing the gene encoding the Neospora protein incorporated into vaccinia virus would comprise stocks of recombinant virus where the gene encoding the Neospora protein is integrated into the genome of the virus in a form suitable for expression of the gene.

EXAMPLES

Example 1

This example describes the isolation and in vitro cultivation of Neospora from aborted bovine fetuses. The isolation of these 2 cultures (BPA1 and BPA2) is described in Conrad et al. *Parasitol.* 106:239–249 (1993). Additional cultures (BPA3–6) were also isolated using the same technique, except that 1 ml (instead of 2 ml) of brain or spinal cord homogenate was trypsinized and then incubated for 2–4 hours, rather than overnight, on the cell monolayer. In addition, the bovine aortic endothelial cell line (CPAE: American Tissue Culture Collection #CCL209) was found to be the best cell monolayer for the cultivation of bovine Neospora. One of these cultures (BPA6) has been shown to induce bradyzoite cysts in mice.

MATERIALS AND METHODS

Pathological Examination and Immunohistochemistry of Fetal Tissues

Aborted bovine fetuses submitted to the California Veterinary Diagnostic Laboratory System were necropsied using standard techniques. The brains from fetuses suspected of having protozoal infections were removed aseptically from the cranium. One half of the brain was placed in sterile saline (0–85% w/v) containing 1000 U/mL penicillin G and 100 µg/mL streptomycin (antibiotic saline) and stored at 4 EC until a diagnosis of protozoal infection was confirmed, at which time the brain could be processed for in vitro cultivation. Multiple tissues, including portions of the brain, liver, kidney, heart, lung, spleen, gastrointestinal tract, skeletal muscle, adrenal gland, trachea and thymus, were collected from each fetus and fixed in 10% neutral buffered formalin for 24 h. Fixed tissues were trimmed, embedded in paraffin, sectioned, stained with hematoxylin and eosin, and examined by light microscopy for the presence of lesions and parasites, as previously described (Barr, et al. 1990 Vet. Pathol. 27:354–61).

Fetuses with multifocal microgliosis and/or necrosis in the brain, suggesting protozoal infection, were further examined by immunohistochemistry for the presence of parasites in brain tissue sections using an avidin-biotin peroxidase complex procedure (Vector Laboratories, Burlingame, Calif., USA) with anti-rabbit serum to detect tissue-binding of rabbit polyclonal anti-N. caninum serum. The immunoperoxidase method employed was basically as described previously (Barr et al. 1991 J. Vet. Diag. Invest. 3:39–46) except that tissue sections were processed using a microprobe system (FisherBiotech, Pittsburgh, Pa., USA) and Probe-On glass slides (FisherBiotech). Aminoethylcarbazole (A.E.C. Substrate System, Dako, Santa Barbara, Calif., USA) was the chromogen.

Parasites in the tissue sections of brains from the 66th and 93rd fetus (hereafter referred to as fetus 66 and 93) were further characterized by the same immunohistochemical procedure to test their reactivity with antisera to additional apicomplexan protozoal parasites. Tissue sections were incubated at room temperature for 1 h with optimal dilutions of the following antisera: 1:1000 dilution of antiserum to N. caninum tachyzoites (Lindsay & Dubey, Am. J. Vet. Res. 50:1981–3(1989)), 1:50 dilution of antiserum to Hammondia hammondi tissue cysts and 4 different antisera to T gondii (Tg1–4). Antiserum Tg1 was produced by the infection of a rabbit with live sporulated oocysts of the ME-49 strain (Lindsay & Dubey, supra) of T. gondii and used at a 1:400 dilution. Toxoplasma gondii antiserum Tg2 (Dr J. C. Boothroyd, Stanford University) was produced by immunization of a rabbit with a tachyzoite lysate of the RH strain of T. gondii and was used at a dilution of 1:300. Antisera Tg3 (BioGenex Laboratories, Dublin, Calif., USA) and Tg4 (I.C.N. Immunobiologicals, Lisle, Ill., USA) were developed by immunizing rabbits with tachyzoites of the RH and H44 strains, respectively. Antiserum Tg3 was applied as supplied by the manufacturer and Tg4 was used at a 1:80 dilution. The optimal dilution chosen for each antiserum produced a strongly positive reaction against the respective positive control parasite with no appreciable non-specific, background staining. Control tissues consisted of paraffin-embedded sections of murine brain with N. caninum tachyzoites, murine brain with T. gondii cysts, murine spleen with T. gondii tachyzoites, murine skeletal muscle with H. hammondi cysts and bovine tongue with Sarcocystis cruzi cysts (Barr et al. Vet. Path. 28:110–116 (1991)).

Parasite Cultures

Stationary monolayer cultures of bovine cardiopulmonary aortic endothelial cells (CPAE: ATCC #CCL209) and M617 bovine macrophages (Speer et al. 1985 Infect. and Immun. 50:566–71) were maintained in Dulbecco's Minimum Essential Medium (DMEM:GIBCO Laboratories, Grand Island, N.Y., USA) supplemented with 10% (v/v) heat-inactivated fetal bovine serum (FBS) or heat-inactivated adult equine serum (HS), 2 mM L-glutamine, 50 U/mL penicillin and 50 µg/mL streptomycin (DMEM-FBS or DMEM-HS). Bovine fetal trophoblast cells (87–3) were grown as previously described by Munson et al. J. Tissue Cult. Methods 11:123–8 (1988)) in DMEM supplemented with 10% (v/v) FBS, 5 µg/mL transferrin, 5 µg/mL insulin, 5 ng/mL selenium, 10 ng/mL epidermal growth factor, 100 µg/mL streptomycin, 100 U/mL penicillin and 0.25 µg/mL amphotericin B (DMEM-FBS*). Control cultures of T. gondii (RH strain provided by Dr J. Boothroyd) and N. caninum (NC1; Dubey el al. J Am Vet Med Assoc 193:1259–1263 (1988)) were maintained in the CPAE and M617 monolayer cultures. Parasite-infected and uninfected monolayer cultures were maintained in 25 or 75 cm$^2$ flasks incubated at 37° C. with 5% $CO_2$. The culture medium was changed 3 times weekly. Established parasite cultures were passaged to uninfected monolayers when 70–90% of cells were infected. To passage parasites, the infected monolayer was removed from the flask by scraping into the media and passed 3 times through a 25-gauge needle to disrupt the cells. The cell suspension was then diluted from 1:2 to 1:8 in fresh complete media and added to a confluent, uninfected monolayer.

After protozoal infection was confirmed by histology, fetal brain tissue that was stored at 4° C. for a variable period of time in antibiotic saline was processed for in vitro cultivation. In all cases where isolates were obtained in vitro, tissue cysts were seen in tissue sections of bovine fetal brain. Half of the fetal brain in approximately 25 mL of antibiotic saline was ground with a pestle and mortar and filtered through sterile gauze. Aliquots of 2 mL of brain homogenate were placed in 10 mL of 0.05% (v/v) trypsin and incubated at 37° C. for 1 h. After trypsin digestion, the material was pelleted by centrifugation at 600 g for 10 min. The supernatant was discarded and the pellet was resuspended in 1–3 ml of either DMEM-HS or DMEM-FBS. Brain from fetus 66 was prepared for culture 48 h after submission and 1 mL of trypsinized brain suspension was dispensed into a 25 cm$^2$ flask of bovine 87-3 trophoblast cells. Brain from fetus 93 was processed 10 days after submission when half of the trypsinized brain was placed in a 25 cm$^2$ flask of 87-3 trophoblast cells and the remainder in a 75 cm$^2$ flask of endothelial cells. After incubation overnight, the brain suspension from both fetuses was removed from the flask and the monolayers were washed 3 times with the appropriate media before adding 5–10 ml of fresh media. Cultures were maintained as described above and examined with an inverted microscope for the presence of parasites.

Immunohistochemistry of Tachyzoites in vitro

Antigenic reactivity of the two in vitro isolates from aborted bovine fetuses was compared to that of tachyzoites from control cultures of T. gondii and N. caninum. Tachyzoites of each isolate were harvested during logarithmic growth by scraping the infected CPAE monolayer from a 25 cm$^2$ tissue culture flask. Monolayer cells were disrupted by repeated passage through a 25-gauge needle. The suspension was passed through a 5 µm filter to remove cellular debris and pelleted by centrifugation at 1500 g for 10 min. After removing the supernatant fraction, the pelleted tachyzoites of each isolate were resuspended in DMEM-HS and inoculated into each of the wells on two 4-chambered tissue culture slides (Lab-Tek, Nunc, Naperville, Ill., USA). Each of the 4 chambers on these slides were seeded 24–48 h prior to parasite inoculation with CPAE cells so that the monolayers were 60–80% confluent at the time of infection. The appropriate slides were inoculated with the slower growing bovine fetal isolates first to allow the parasites to grow for 48 h, whereas the isolates of *T. gondii* and *N. caninum* were cultivated on slides for 24 h before being processed for immunohistochemical evaluation.

To prepare the parasite cultures for immunohistochemistry, culture supernatants were removed with monolayers remaining adherent to glass slides. These slides were fixed in 100% methanol (4° C.) for 10 min and allowed to air dry completely before being washed 3 times for 5 min each in physiologically buffered saline (PBS:pH 7.2), incubated for 10 min in 3% (v/v) hydrogen peroxide in methanol, washed again 3 times for 5 min each in PBS and incubated for 30 min with 20% goat serum to block non-specific antibody binding sites. Each slide was then incubated for 1 h with 3 wells containing different primary antiserum and 1 well serving as a negative control with a pre-infection rabbit serum. The optimal antisera dilutions were selected to produce a strongly positive reaction against the homologous culture-derived antigen with no appreciable non-specific, background staining. The dilutions of antisera used for staining parasites in vitro were 1:3000 for *N. caninum*, 1:800 for Tg1, 1:40 for Tg2, 1:1 for Tg3, 1:2000 for Tg4 and 1:50 for *H. hammondi*. Slides were washed 3 times for 5 min each in PBS and the secondary antibody and conjugate were applied as described above for the tissue sections except that the slides were processed manually and the chromogen was applied for only 2 min.

RESULTS

The first parasite isolate (BPA1) was obtained from fetus 66 which was estimated to be approximately 4 months gestational age and in relatively good postmortem condition at the time of necropsy. Significant gross lesions were restricted to focal epicardial petechiae. On histological examination there were infrequent, random, small foci of gliosis and 5 protozoal cysts were seen in sections of the fetal brain. The tissue cysts ranged from 8 to 10 $\mu$m in diameter and had distinct, thin walls (<1 $\mu$m) surrounding at least 25–40 closely packed bradyzoites. In addition there were scattered mononuclear inflammatory cell infiltrates in the heart, portal tracts of the liver and throughout the renal cortex. In the lung, macrophages and neutrophils were present within alveolar septa, adjacent to bronchioles and free in the lumen of bronchioles and alveoli. *Escherichia coli* and *Proteus* spp. were isolated from the lung, liver, spleen and abomasal contents of this fetus.

The second isolate (BPA2) was obtained from fetus 93 which had an estimated gestational age of 6 months and was mildly autolyzed. Histological examination revealed infrequent random foci of gliosis in the brain with adjacent capillaries that had prominent hypertrophied endothelium. There was also a mild diffuse meningeal infiltrate of mononuclear cells, consisting predominantly of lymphocytes with occasional plasma cells. Four randomly located protozoal tissue cysts were found in the brain; one being located adjacent to a focus of gliosis. The cysts were 8–13 $\mu$m in diameter with at least 25–50 bradyzoites. Two of the cysts had thick (1–2 $\mu$m) walls. Focal, mixed mononuclear inflammatory cell infiltrates were also present in skeletal muscle and in the renal cortex.

Table 1 summarizes the immunoreactivity of protozoal tissue cysts in the brains of fetus 66 and fetus 93 with different polyclonal antisera and compares these antigenic reactions to those of *N. caninum, T. gondii, H. hammondi* and *S. cruzi*. The protozoal cysts in fetuses 66 and 93 reacted most strongly to *N. caninum* antiserum and had weaker reactions to *H. hammondi* antiserum. With both antisera, staining was predominantly to the cyst wall with some staining of zoites within the cysts. Overall, the reactivity of cysts in the two bovine fetuses was more similar to the reactivity of *N. caninum* tachyzoites than to that of *T. gondii* tachyzoites or cysts, *H. hammondia* cysts or *S. cruzi* cysts.

TABLE 1

Reactivity of tissue cysts and tachyzoites with rabbit polyclonal antisera against different parasites in an immunoperoxidase test

|  |  |  |  | Antisera |  |  |  |
|---|---|---|---|---|---|---|---|
|  |  | Neopora | Hammondia | \multicolumn{4}{c}{Toxoplasma gondii} |
| Parasite antigen | Tissue | caninum | hammondi | Tg1 | Tg2 | Tg3 | Tg4 |
| Fetus 66 cysts | Bovine brain | ++* | ++* | " | – | – | – |
| Fetus 93 cysts | Bovine brain | ++* | +* | – | – | – | – |
| *Neospora caninum* tachyzoites | Mouse brain | +++ | – | ++ | – | – | – |
| *Toxoplasma gondii* tachyzoites | Mouse spleen | – | ++ | +++ | +++ | " | " |
| *Toxoplasma gondii* cysts | Mouse brain | + | +++ | +++ | + | ++ | ++ |
| *Hammondia hammondi* cysts | Mouse muscle | " | +++ | +++ | – | + | ++ |
| *Sarcocystis cruzi* cysts | Bovine muscle | – | – | – | – | – | – |

*Primarily cyst wall staining

In approximately 14 months, over 100 fetuses were submitted specifically as protozoal abortion suspects from dairies in California. Parasite isolations were attempted with brains from the 49 fetuses which had Neospora-like protozoa identified by immunohistochemistry. The first evidence of parasite growth in these cultures was detected in the 87-3 cell line 34 days after inoculation of brain tissue from fetus 66 (isolate BAP1). The next successful in vitro isolation was apparent when tachyzoites were first observed in 87-3 and CPAE cultures on day 15 after inoculation with brain tissue from fetus 93 (isolate BPA2). In cultures of both isolates, parasites first appeared as small clusters of intracellular tachyzoites in pairs or random groups. Extracellular tachyzoites were seen escaping from the bovine cell monolayers and moving by gliding and twisting in the culture medium. On Giemsa-stained smears of infected monolayers, extracellular tachyzoites were 1.5–2.5 µm wide at the nucleus and 6–8 µm long. The number of tachyzoite clusters and number of tachyzoites in each cluster increased gradually in the cultures as they became established with continuous parasite growth. Generally, parasite clusters contained approximately 10–100 tachyzoites. Growth of both isolates was maintained in cultures of 87-3, CPAE, or M617. However, the best growth was observed in the 87-3 and CPAE cultures. Within 2–3 months of establishment, the cultures were passaged weekly whenever approximately 80–95% of the bovine monolayer cells were infected with tachyzoites. Routinely, the established BPA1 and BPA2 cultures were passaged by adding a 1:8 dilution of needle-passaged monolayer in fresh media to cultures of uninfected bovine monolayers. By comparison, in our laboratory, cultures of *T. gondii* (RE isolate) are routinely passaged at a 1:200 dilution and *N. caninum* (NC-1 isolate) cultures are passaged at a 1:10 dilution every 2–3 days. As of mid-May 1992, cultures of the BPA1 and BPA2 isolates had been maintained with continuous growth for 10 and 6 months, respectively.

The results of an antigenic comparison of in vitro cultivated tachyzoites of BPA1 and BPA2 to those of cultivated *N. caninum* and *T. gondii* tachyzoites are shown in Table 2. The reactions of the bovine fetal isolates to the different antisera were similar to that demonstrated by *N. caninum*, and distinctly different from the pattern of reactivity observed with *T. gondii* tachyzoites (Table 2).

TABLE 2

Reactivity of in vitro cultivated tachyzoites with rabbit polyclonal antisera against different parasites in an immunoperoxidase test

| Parasite antigen | Antisera | | | | | |
|---|---|---|---|---|---|---|
| | *Neospora caninum* | *Hammondia hammondi* | \multicolumn{4}{c}{*Toxoplasma gondii*} |
| | | | Tg1 | Tg2 | Tg3 | Tg4 |
| Fetus 66 (BPA1) | +++ | – | – | + | – | – |
| Fetus 93 (BPA2) | +++ | – | " | + | – | – |
| *Neospora caninum* | +++ | – | – | + | – | – |
| *Toxoplasma gondii* | – | +++ | +++ | +++ | +++ | +++ |

By transmission electron microscopy, the in vitro tachyzoites of isolates BPA1 and BPA2 were morphologically similar. Therefore, the following ultrastructural description applies to both isolates. Individual tachyzoites or clusters of multiple tachyzoites were usually located within a parasitophorous vacuole in the cytoplasm of bovine monolayer cells. Tachyzoites had a pellicle consisting of a complex of 2 inner membranes beneath a plasmalemmal membrane, a prominent nucleus in the central or posterior portion of the tachyzoite, 1 to 3 profiles of long tubular cristate mitochondria, a Golgi complex, rough and smooth endoplasmic reticulum, single- or multiple-membraned vesicles, and numerous free ribosomes. Ultrastructural apical features characteristic of apicomplexan parasites were present in tachyzoites of both isolates, including a polar ring which gave rise to 22 longitudinal subpellicular microtubules, a cylindrical or cone-shaped conoid within the polar ring and numerous electron dense rhoptries. The number of rhoptries visible in individual tachyzoites varied greatly and was dependent to some extent on the plane of section. A maximum of 24 rhoptries was counted in the anterior end of transversely sectioned tachyzoites. Rhoptries were not seen posterior to tachyzoite nuclei. In longitudinal sections, rhoptries were elongated, club-shaped structures with narrow, dense necks that extended into the conoid. As many as 14–32 electron-dense bodies were observed primarily posterior to the nucleus. Smaller numbers of these dense bodies were found anterior to the nucleus. Unlike rhoptries, dense bodies were generally round or oval in longitudinal sections. Large numbers of micronemes were seen in the anterior end of tachyzoites and only rarely observed posterior to the nucleus. The micronemes were most often arranged in organized arrays or sheets that were orientated parallel to the pellicular membrane or longitudinal axis of the tachyzoite. The number varied greatly in individual tachyzoites but as many as 60–100 micronemes were counted in longitudinal or oblique sections of selected tachyzoites. In addition, a single micropore, located anterior to the nucleus was seen in some tachyzoites. Parasites multiplied by endodyogeny and many were observed in the process of forming 2 progeny zoites within a single tachyzoite. Rarely, as many as 4 zoites with intact nuclei were seen in division but still attached to each other at the posterior end.

A concerted effort focused on the in vitro isolation of Neospora-like protozoal parasites from cattle after studies showed that they were the major diagnosed cause of abortion in California dairy cattle. Histologically, the two bovine fetuses from which isolates were first obtained in 1991 had compatible lesions, including multifocal non-supportive encephalitis, and protozoal tissue cysts like those seen in other natural infections of Neospora-like protozoa in bovine fetuses. The immunological reactivity of tissue cysts in the brains of fetus 66 and fetus 93 was also similar to that seen with many of the cysts in naturally infected fetuses which had strong reactions with *N. caninum* and *H. hammondi* antisera and occasional reactions to some of the *T. gondii* antisera.

Isolation of these Neospora-like protozoal parasites from aborted bovine fetuses was difficult because fetuses are generally moderately to severely autolyzed at the time of abortion and protozoal tissue cysts are present in a relatively small proportion of the infected fetuses. Previous ultrastructural studies suggested that most of the protozoal cysts in these fetal tissues were affected by autolysis and were probably non-viable (Barr el al. 1991 *Vet. Path.*28:110–16). The two fetuses from which isolates were obtained were in comparatively good postmortem condition. This fact, plus the relatively large number of cysts in these fetuses may have been critical factors in the successful isolation of the protozoal parasites. In addition, the isolation methods were modified. In particular, a longer period of trypsinization in preparing the brain material for cultivation, the overnight incubation of the brain homogenate on the monolayer, and use of the 87-3 bovine trophoblastic cell line for the initial parasite isolation were modifications in these procedures which appeared to be particularly helpful in obtaining the BPA1 and BPA2 isolates. Parasite growth was best maintained in 87-3 and CPAE monolayer cells. This contrasts with *N. caninum* and *Hammondia heydorni* which are reported to grow better in bovine monocyte cells (Speer et al. 1988 *Infect. and Immun.* 50:566–71).

In comparing these bovine protozoal isolates to those of *T. gondii* and *N. caninum* that have been re-isolated from mouse brains, it was found that the bovine protozoal isolates grew more slowly during isolation and after establishment of continuous growth. Whether this reflects a difference in the virulence of the organisms or a difference in adaptation to culture remains to be determined.

By light microscopy, tachyzoites of the bovine isolates were morphologically similar to in vitro tachyzoites of *T. gondii* and *N. caninum*. Cultivated tachyzoites of the bovine isolates had similar immunohistochemical reactions to tachyzoites of *N. caninum*, reacting strongly with *N. caninum* anti-serum and weakly to serum Tg1 which was produced by immunization of a rabbit with tachyzoite lysates of *T. gondii*. These antigenic reactions were distinctly different from those seen with culture-derived tachyzoites of *T. gondii*. Differences in antigenic reactivity of the cultivated BPA1 and BPA2 tachyzoites, as compared to those of tissue cysts in the source fetuses, could be explained by the stage-specific antigen expression of the different parasites and variations in the methods used to produce the antisera (i.e. immunization with cysts, oocysts or tachyzoite lysates). For example, tissue cyst wall antigens that reacted with antiserum to *H. hammondi* appeared to be lacking on tachyzoites of the bovine isolates in vitro. Unfortunately, a direct comparison of different parasite stages was not always possible since tachyzoites were not identified in the brains of the two bovine fetuses and true cysts have not been observed in the BPA1 or BPA2 cultures. Similarly, *N. caninum* tissue cysts and culture-derived *H. hammondi* tachyzoites were not available for comparison. Differences in antigenic expression may also be affected by host-specific factors. To evaluate this possibility, efforts are under way to obtain material from cattle, dogs, rats, cats and mice that have been experimentally infected with *N. caninum* or the bovine isolates so as to make a direct comparison of antigenic reactivity of the parasites in the same host species.

Thus far, characterization of the in vitro isolates from the two aborted bovine fetuses has shown that these parasites are antigenically and/or ultrastructurally distinct from *T. gondii*, *H. hammondi*, *S. cruzi*, Besnoitia spp. and Frenkelia spp. These isolates most closely resemble *N. caninum* parasites which have been most extensively studied in the USA and Scandinavia. The similarity between these parasites indicates that the BPA1 and BPA2 isolates belong to the genus Neospora. At present little is known about the lifecycle, including the definitive host, of these Neospora parasites in dogs or cattle. A better understanding of the biology of these parasites is essential to determine their taxonomic relationship to each other and to other apicomplexan parasites.

Example 2

This example describes an indirect fluorescent antibody (IFA) test for the detection of parasite-specific antibody responses in cattle that were naturally or experimentally infected with Neospora parasites. The methods used here are generally as described in Conrad et al. 1993 *J. Vet. Diagn. Invest.* 5:572–578 (1993).

MATERIALS AND METHODS

Parasites and Antigen Slide Preparation

Antigen slides were prepared using tachyzoites of the BPA1 described above. Culture media consisted of Dulbecco's Minimum Essential Medium (DMEM) supplemented with 10% (v/v) heat-inactivated adult equine serum, 2 mM L-glutamine, 50 U/mL penicillin and 50 ug/mL streptomycin (DMEM-HS). Tachyzoites of *Toxoplasma gondii* (RH isolate; kindly provided by Dr. J. Boothroyd) were obtained from CPAE monolayer cultures grown in the same medium except that 10% (v/v) heat-inactivated fetal bovine serum was used instead of equine serum. Parasite-infected cultures were maintained in 25 or 75 cm$^2$ flasks incubated at 37EC in an atmosphere of 5% $CO_2$.

Parasites were harvested for antigen preparation when approximately 80% of the CPAE cells in the culture flask were infected with clusters of tachyzoites. The infected monolayer was removed from the flask by scraping into the medium and then passed 3× through a 25 gauge needle to disrupt the cells. The suspension was passed through a 5$\mu$m filter to remove cellular debris and tachyzoites were pelleted by centrifugation at 1300×g for 10 min. After removing the supernatant, the pellet was washed twice in sterile phosphate buffered saline pH 7.2 (PBS) and then resuspended in a modified PBS saline (137 mM NaCl, 3 mM KCl, 3 mM $Na_3C_6H_5O_7.2H_2O$, 0.4 mM $NaH_2PO_4.H_2O$, 12 mM $NaHCO_3$, 6 mM glucose) to a final concentration of approximately 2,000 tachyzoites/$\mu$L. Aliquots of 10 $\mu$L of tachyzoite suspension were dispensed into each 4 mm well on 12-well heavy teflon coated (HTC) antigen slides. Slides were air-dried at room temperature and stored at −70° C.

Cattle

Test sera was obtained from naturally infected cows that aborted Neospora-infected fetuses, as well as congenitally infected calves. In addition, sera was obtained from two pregnant heifers that were experimentally infected at approximately 120 days gestation with tachyzoites of the BPA1 isolate derived from CPAE cultures. Tachyzoites were obtained from cultures using the procedure described for harvesting tachyzoites for antigen preparation except that the parasites were not washed in PBS and only the inoculum given to each heifer intravenously was filtered to remove cellular debris. After centrifugation, tachyzoites were resuspended in DMEM and administered by inoculation to each heifer so that 3×10$^6$ tachyzoites were given IV and 5×10$^6$ were given IM. A control heifer from the same herd and at the same stage of gestation was inoculated with an equivalent amount of uninfected CPAE cell culture material which was prepared and administered using the same procedures as for the infected heifers. Natural or experimental infections were confirmed by identification of Neospora tachyzoites and/or tissue cysts in fetal or calf tissues using an immunoperoxidase test procedure (Anderson, et al., *J Am Vet Med Assoc* 198:241–44 (1991) and Barr, et al, *Vet Path* 28:110–116 (1991)).

For serological comparison with samples from Neospora-infected cattle, sera were obtained from the following additional sources: 1) cows that aborted fetuses which did not have lesions or parasites typical of Neospora infections, 2) weak calves that were suspected of having Neospora infections, but showed no lesions or parasites on post-mortem histopathologic examination, 3) 20 heifers that were purchased as weanlings from a closed beef herd in Todd County, Nebr. and maintained under strict isolation, on range conditions at the Agricultural Research Development Center, University of Nebraska-Lincoln in Mead, Nebraska, 4) 20 pregnant heifers that were maintained on pasture in California and 5) 21 adult beef bulls or cows that were originally on pasture and then maintained in the same feedlot as the experimentally infected heifers.

Serum Collection and Testing

Test and control sera were obtained from blood samples that were collected by venipuncture into vacutainer tubes without anticoagulant. After storage at 4° C. for 2–12 hr, the blood was centrifuged at 500×g for 10 min and the serum was removed. Sera was stored either at 4° C. for <48 hr or frozen at −70° C. until tested.

Antigen slides were thawed at room temperature immediately prior to use. Sera were initially titrated in 2-fold dilutions from 1:40 to 1:40,960 to determine the end-point titer. Ten µL of diluted test or control sera were placed in separate wells on the antigen slides. Slides were incubated at 37° C. for 1 hr in a moist chamber, washed 3× for 5 min each in PBS, and then tapped gently to remove excess PBS. Fluorescein-labeled affinity-purified rabbit anti-bovine IgG diluted 1:500 in PBS was added in 10 µL aliquots to each well. Slides were incubated at 37° C. for 30 min, washed 3 times with PBS for 5 min each wash, tapped to remove excess PBS, cover-slipped with buffered glycerol (25% [w/v] glycerin in TRIS-HCl: pH 9.0), and examined at 200 magnification using a fluorescence microscope. The end-point titer was the last serum dilution showing distinct, whole parasite fluorescence.

RESULTS

Natural Infections

Sera collected at the time of abortion from 64 cows were tested for serologic reactivity to Neospora antigen (isolate BPA-1) using the IFA test procedure. Aborted fetuses from 55 of these cows had nonsuppurative encephalitis and/or myocarditis which was consistent with a protozoal infection. In addition tachyzoite and/or cyst stages of Neospora were identified by immunohistochemistry in the tissues of these 55 fetuses (Table 3). In the remaining 9 fetuses there was no indication of encephalitis and/or myocarditis and no detectable protozoal parasites. All of the cows that aborted Neospora-infected fetuses had titers of 320 to 5,120 to Neospora antigens (Table 3). Eight of the cows that aborted fetuses with no detectable Neospora parasites had titers #160 and one had a titer of 320.

TABLE 3

Titers of cow sera collected after abortion of Neospora-infected fetuses to bovine Neospora (BPA1 isolate) antigens.

| Neospora titer | Number of cows | Neospora tissue stages in fetus | | |
|---|---|---|---|---|
| | | cysts | tachys | cysts & tachys |
| 320 | 1 | 0 | 1 | 0 |
| 640 | 12 | 2 | 8 | 2 |
| 1280 | 12 | 2 | 10 | 0 |
| 2560 | 15 | 2 | 11 | 2 |
| 5120 | 15 | 5 | 7 | 3 |

Figure 2:
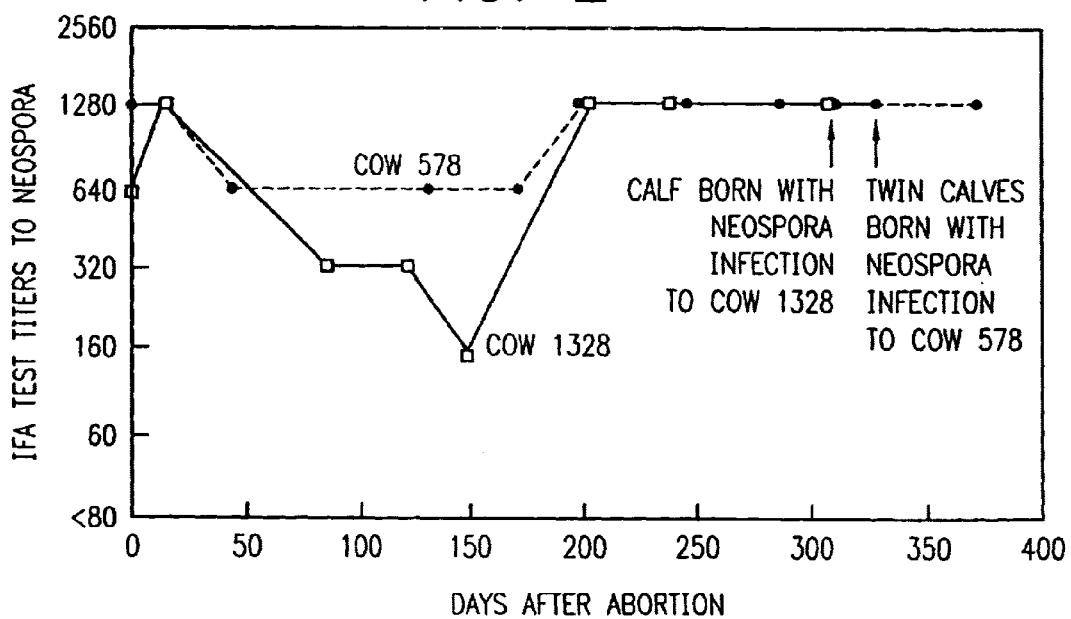
FIG. 2 shows IFA test titers of serial samples from two cows that aborted Neospora-infected fetuses and subsequently delivered congenitally infected calves.

Six of the cows that aborted Neospora-infected fetuses were maintained on their 4 dairies of origin so that these cows could be tested repeatedly over a 6 to 12 month period to determine changes in the Neospora titer. Peak titers of 640 to 2,560 were apparent within the first 20 days after abortion in all of the cows (FIGS. 1 & 2). Subsequently, the titers of 4 of the cows (FIG. 1, cows 9, 970 & 522; FIG. 2, cow 578) decreased to 640, whereas the titers of cow 3 (FIG. 1) and cow 1328 (FIG. 2) dropped to 160 within 150 days post-abortion. Cows 578 and 1328 were rebred and became pregnant again within approximately 50 to 70 days of aborting Neospora-infected fetuses. When these cows were approximately 4 to 5 months pregnant their Neospora titers increased to their original peak levels of 1,280 and remained at this level until the cows gave birth to full-term calves (FIG. 2). The calf born to cow 1328 had a pre-colostral titer of 20,480 and twin calves born to cow 578 both had precolostral titers of 10,240 to the bovine Neospora isolate. Upon necropsy at 2 to 6 days of age, these calves showed mild nonsuppurative encephalomyelitis or focal mononuclear cell infiltrates the brain parenchyma. Neospora tissue cysts were seen in association with inflammatory lesions in all 3 calves. The post-colostral titers of sera taken from each calf prior to euthanasia were the same as their preco-lostral titers.

Serologic titers were determined for four additional calves that were diagnosed as having congenital Neospora infections based on the presence of characteristic cyst stages in the brain and/or spinal cord which reacted immunohistochemically with antisera to the BPA-1 bovine Neospora isolate. Neospora was isolated from the brains and/or spinal cords of calves 1–3 and the parasites were grown continuously in vitro, using a previously described method for isolation of Neospora from aborted bovine fetuses. At necropsy, calves 1 and 2 had Neospora titers of 20,480, calf 3 had a titer of 10,240 and calf 4 had a titer of 5,120. Sera collected from the dam of calf 4 at calving had a Neospora titer of 2,560. Precolostral calf sera and sera from the dams of calves 1–3 were not available for testing.

The titers observed in the 7 congenitally infected calves with confirmed Neospora infections were markedly greater than those obtained with sera from 4 weak 1–5 day old calves which were suspected of having Neospora infections, but showed no histopathologic evidence of characteristic lesions or parasites on post-mortem examination. One of these uninfected calves had a titer of 160, while the others had titers <80 to bovine Neospora antigens. Whether or not these calves had received colostrum was not known.

Experimental Infections

Figure 3:
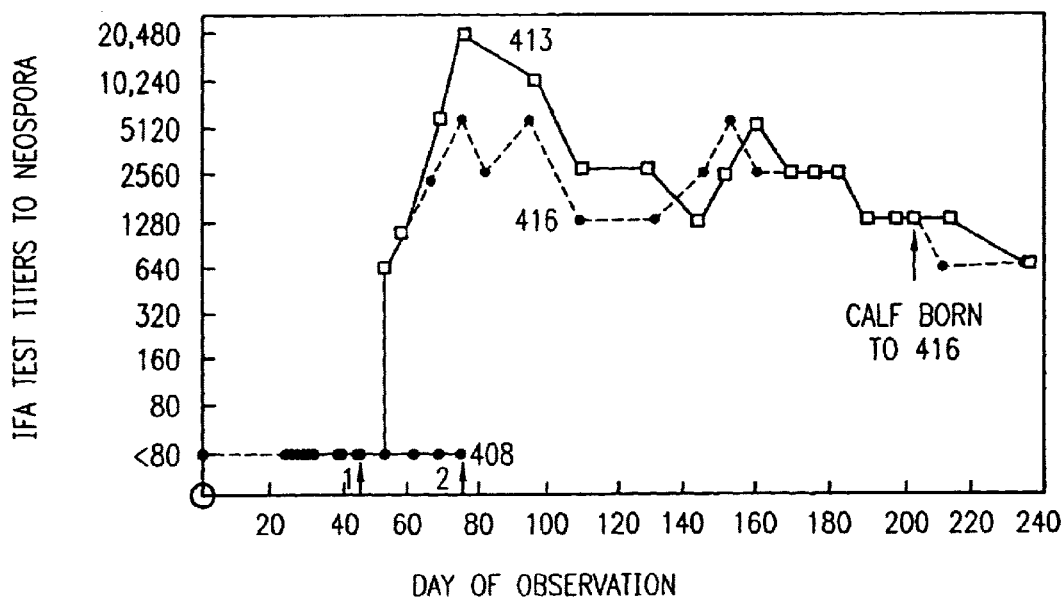
FIG. 3 shows seroconversion by heifers experimentally infected with Neospora.

Repeated sera samples taken from the 3 pregnant heifers prior to experimental inoculation on day 43 had titers of <80 to Neospora BPA1 antigens. The 2 heifers that were infected with culture-derived tachyzoites of the BPA1 bovine isolate developed Neospora titers of 640 by day 9 and 1,280 by day 18 after parasite inoculation (FIG. 3). The heifer that received uninfected cell culture material had titers <80 to Neospora antigens throughout the experiment. She was euthanitized 32 days after inoculation to remove her fetus which was viable, histologically normal and uninfected, with no detectable titer to Neospora. Peak titers for both infected heifers were detected 32 days after parasite inoculation, at which time the fetus of heifer 413 was removed by caesarian section. Histologically, the fetus had inflammatory lesions and numerous Neospora tachyzoites present in its central nervous system. In addition, Neospora tachyzoites were isolated from fetal tissues and grown continuously in cell culture. Sera collected from the fetus had a titer of 640 to Neospora antigens. After her fetus was removed, the Neospora titer of heifer 413 fluctuated between 1,280 and 5,120, until day 193 post-infection when it dropped to 640 (FIG. 3). Heifer 416 calved 158 days after parasite inoculation at which time she had a Neospora titer of 1,280 (FIG. 3). The calf had a precolostral Neospora titer of 10,240 which was the same as the sample which was collected 2 days later, after ingestion of the dam's colostrum. Clinically the calf appeared normal except that it had decreased conscious proprioception in all 4 limbs when examined prior to euthanasia at 2 days of age. There were minimal histological lesions, consisting of focal gliosis in the central nervous system, but no parasites were detected in fetal tissues.

Uninfected Cattle

Fifty three of the 61 (87%) adult cattle tested which had no history of Neospora infection had titers #80, and all but one animal had titers #160 to both Neospora and Toxoplasma antigens (Table 4). The pastured cattle that were moved and subsequently maintained under feedlot conditions did not have higher serologic titers to tachyzoites of bovine Neospora or *Toxoplasma gondii* than those kept on pasture. End-point titer determinations of all samples from infected or uninfected cattle were always based on whole tachyzoite fluorescence. However, in testing the apparently uninfected animals, sera samples from 3 of the cows and 7 of the bulls that were housed in the feedlot at the University of California at Davis (UCD feedlot) had parasite fluorescence which was restricted to the apical end of the parasite. This reaction was particularly marked with the 7 sera from bulls which had apical fluorescence titers of 160 to 320 to both Neospora and Toxoplasma, while the whole parasite fluorescence titer was #80.

TABLE 4

Titers of sera from cattle with no evidence of Neospora infection to bovine Neospora (BPA1 isolate) and *Toxoplasma gondii*.

| Cattle | Location | Neo. titer | Number positive | Toxo. titer | Number positive |
|---|---|---|---|---|---|
| 20 heifers | Nebraska pasture | ≦80 | 16 | ≦80 | 14 |
|  |  | 160 | 3 | 160 | 6 |
|  |  | 320 | 1 |  |  |
| 20 heifers | California pasture | ≦80 | 17 | ≦80 | 13 |
|  |  | 160 | 3 | 160 | 3 |
|  |  |  |  | ND | 4 |
| 9 cows | UCD* feedlot | <80 | 9 | ≦80 | 7 |
|  |  |  |  | 160 | 2 |
| 12 bulls | UCD feedlot | ≦80 | 11 | ≦80 | 10 |
|  |  | 160 | 1 | 160 | 2 |

*University of California, Davis, California

Figure 4:
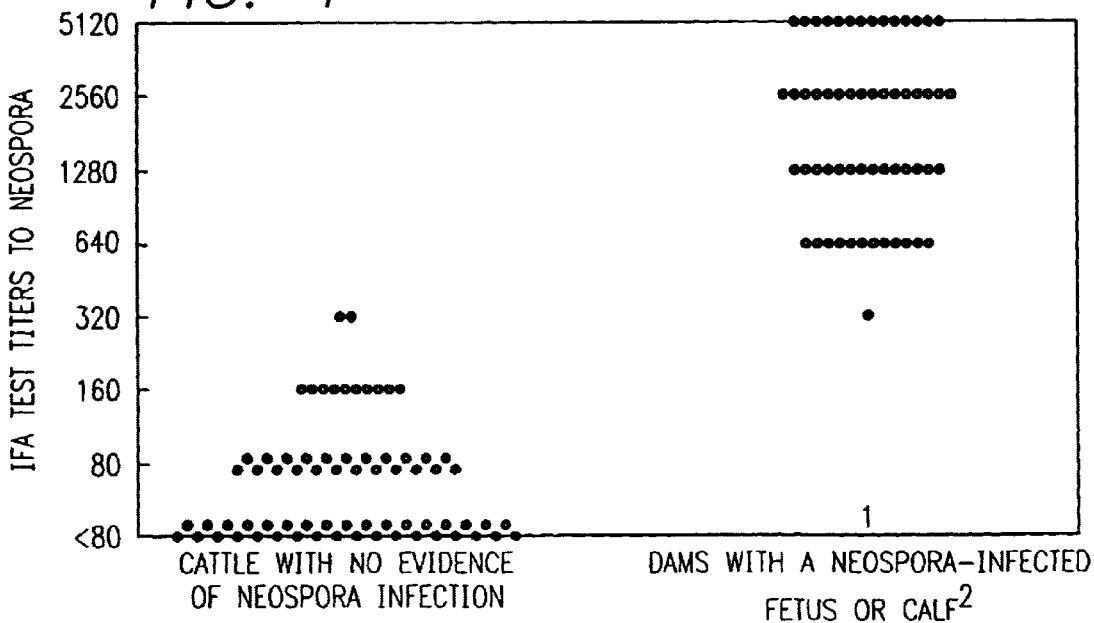
FIG. 4 shows IFA test titers: comparing cattle with no evidence of infection to dams with Neospora-infected fetuses or calves.

FIG. 4 shows the serologic titers of the 61 uninfected adult cattle plus the 9 cows that aborted fetuses without evidence of Neospora infections compared to the titers of Neospora-infected cows at the time of abortion or calving. Although a majority of the infected cattle had titers $1280 to Neospora and most of the cattle that had no evidence of infection had titers #80, there was some overlap between these groups from the 160 to 640 titer range (FIG. 4).

Example 3

This example describes isolation of DNA encoding nss-rRNA (SEQ ID NO 1).

Parasites

Bovine Neospora isolates BPA-1 BPA-2, BPA-3, BPA-4, BPA-5 were used for DNA isolation. Parasites were harvested for DNA preparation when >80% of the CPAE cells were infected with large clusters of tachyzoites. The infected monolayer was removed from the flask by scrapping. The tachyzoites in tissue culture media were pelleted by centrifugation at room temperature, 1300×g for 10 minutes. The supernatant was removed and the pellet was resuspended in 10 mL sterile physiologically buffered saline (PBS: pH 7.4), passed through a 25 gauge needle three times to disrupt the CPAE cells, and then filtered through a 5 $\mu$m disc filter (Gelman Sciences, Acrodisc) to remove cellular debris. The filtered material was pelleted at 1300×g for 10 minutes and washed in PBS (pH 7.4). The supernatant was removed and the tachyzoite pellet was stored at −70° C. until used.

Uninfected CPAE monolayer cells were processed by the same procedure and used as controls.

Two methods were used to prepare the DNA from the tachyzoites and control CPAE cells. Initially, DNA was prepared as follows. Briefly, the parasite or control cell pellets were suspended in 1.0 ml STE with 0.5% SDS treated with proteinase K (100 $\mu$g/mL) and RNAase (100$\mu$g/mL) then extracted twice with phenol, once with phenol-chloroform-isoamyl alcohol, and once with chloroform-isoamyl alcohol. DNA was subsequently precipitated with ethanol, dried and resuspended in TE buffer. Other DNA samples were prepared with the Isoquick DNA Extraction kit (Microprobe, Corp., Garden Grove, Calif.) following manufacturer's directions.

DNA preparations were electrophoresed in 0.8% (w/v) agarose (FMC) Bioproducts) in 0.5 M Tris/borate/EDTA (TBE) buffer (89 mM Tris, 89 mM boric acid, 2 mM EDTA) gels stained with ethidium-bromide (0.5 ug/ml) and examined under ultraviolet (UV) light.

Amplification of rRNA Gene Sequences

DNA sequences were amplified by the polymerase chain reaction (PCR) using a programmable thermal cycler (Perkin-Elmer). Reactions were performed in 50 to 100 $\mu$L volume samples containing approximately 50–100 ng of DNA template, 50 mM Tris buffer (pH 8.3), 1 .0 mM MgCl$_2$, 200 mM of each of the four deoxynucleoside triphosphates, 0.5 U of Taq polymerase (Promega) and 100 pM of universal primer A (5'CCG AAT TCG TCG ACA CCT GGT TGA TCC CCG ACG ACC GTG GTC TGA ACG GGA G' (SEQ ID NO 2)) and primer C (5'GGG CCC TAG GTG GCG CCG ACG ACC GTG GTC TGA ACG GGA G 3' (SEQ ID NO 3). The PCR cycling parameters consisted of a single step at 94° C. for 3 minutes followed by 30 cycles denaturation at 94° C. for 1 minute, 1 minute of annealing at 55° C., and 2 minutes of extension at 72° C. with a final extension step of 7 minutes. The PCR amplification product was an approximately 550-bp sequence from the 5' end of the nss-rRNA gene. A more extensive 1.8 kb sequence of the nss-rRNA gene was amplified from BPA1 DNA using universal primer A and primer B (5'CCC GGG ATC CAA GCT TGA TCC TTC TGC AGG TTC ACC TAC 3' (SEQ ID NO 4)).

These reactions were performed using 50 $\mu$L reaction samples that contained 100 pM of each primer, 1 mM MgCl$_2$, 50–100 ng of template DNA, 50 mM Tris buffer (pH 8.3), 1.0 mM MgCl$_2$, a 200 mM of each of the four deoxynucleoside triphosphates (dATP, dCTP, dGTP, and dTTP), and 0.5 U of Taq polymerase (Promega). The amplification cycles were performed by an initial denaturation step at 94° C. for 3 minutes followed by 45 cycles of denaturation at 94° C. for 1 minute, 1 minute of annealing at 55° C., and 4 minutes of extension at 72° C. with the final extension step for 7 minutes. For both amplification reactions, the stationary CPAE cell DNA was used as the negative template control. Sterile water was used for the PCR reaction condition controls. Aliquots of each PCR product were sized by comparison with DNA standards (Bioventures, Inc. TN) after electrophoresis through a 3% (w/v) NuSieve, 1% (w/v) SeaKem agarose gel (FMC BioProducts, Rockland Me.) stained with ethidium bromide and visualized under UV light.

Amplification products from 3 to 5 reactions were pooled prior to purification to reduce the possibility of any nucleotide misincorporation errors by the Taq polymerase during the elongation step of the newly synthesized complement strain. The PCR amplification products were purified either by gel electroelution or by spin-columns. Two different spin-columns were used at different times. First, Magic PCR Prep DNA purification System (Promega Corp.) was used following manufacturer's directions. Briefly, the products were electrophoresed through a low temperature melting agarose (Low, Melt Agarose, FMC BioPorducts,). The DNA was visualized in the gel by ethidium bromide staining and the DNA band was excised into an eppendorf tube. The agarose and DNA were heated (70° C.) to melt the agarose. The DNA was separated from the agarose using columns and reagents provided in the kit. Later simpler and less time intensive methods were used by purifying the PCR products using the PCR Select II (5 Primer-3 Prime, Inc) columns which do not require electrophoresis and excision of the product in low melt agarose.

DNA sequencing of the purified PCR products were performed following manufacturer's instructions for the PCR Cycle Sequencing System (BRL ds DNA Cycle Sequencing System). The cycling parameters consisted of a two step program after complete denaturation at 95° C. for 3 minutes. The first program step amplified DNA using 20 cycles that included 30 seconds for denaturation, 30 seconds for annealing, and 1 minute of extension. The second program step alternated between denaturation (95° C.) and extension (72° C.) only. Initially, the universal primers (A, C or B) were used to obtain the first nucleotide sequence data from which internal primers could be constructed and used to amplify internal sequences. All sequencing primers were 5' labeled with adenosine $5'[\gamma^{32}P]$ triphosphate (Amersham). Reactions were heated to 95° C. for 5 minutes prior to loading onto either a 6% (w/v) or 8% (w/v) polyacrylamide, 8 M urea (0.4 mm thick) non-gradient gel using a Model S2 Sequencing Gel Apparatus (GIBCO BRL, Gaithersburg, Md.). The sequencing gels were fixed in 10% acetic acid and 10% methanol to remove the urea prior to transfer of the sequencing products in the gel onto filter paper. The gels were dried using a gel drying apparatus (Biorad Gel Drier, X) for 1 to 2 hours at 70–80° C. The membrane filters were autoradiographed using Kodak X-OMAT X-ray film.

DNA Sequence Analysis

DNA sequences were constructed from at least 3 separate reactions to ensure the accuracy of the nucleotide sequence data obtained. Autoradiographs of the sequencing products were read using Hibio MacDNASIS DNA and Protein Sequence Analysis System (Hitachi Software Engineering Co,). This program and the GCG programs (SEQED, Fragment Assembly, Lineup, and Pretty) (University of Wisconsin Genetics Computer Group) on a VMS system facilitated the construction of the DNA sequences.

Example 4

This example describes the design of primers and brobes for detection of Neospora DNA.

Oligonucleotide PCR Primers
(1) Bovine Neospora Forward Primer
 (5'-AAGTATAAGCTTTTATACGGCT-3' (SEQ ID NO 5))
2) Bovine Neospora Reverse Primer
 (5'-CACTGCCACGGTAGTCCAATAC-3' (SEQ ID NO 6))

DNA amplification was carried out in a total volume of 50 µL. The reaction mixture contained 10 mM Tris-HCl (pH 9.0), 50 mM potassium chloride, 0.1% Triton X-100, 1.0 mM magnesium chloride, 200 mM of each deoxynucleoside triphosphates, 0.42 µM Bovine Neospora Forward primer and 0.384 µM Bovine Neospora Reverse primer. After precycle denaturation at 94° C. for 4 min to reduce nonspecific amplification, 2.5 U of Taq DNA polymerase (Promega Corp., Madison, Wis.) were added and the mixture was overlaid with 50 µL of mineral oil. Amplification was performed in a DNA Thermal Cycler (Perkin Elmer Cetus Corp., Norwalk, Conn.) for 31 cycles as follows: denaturation at 94° C. for 1 min, annealing at 54° C. for 1 min, and extension at 72° C. for 2 min. The last cycle was given a prolonged extension period of 7 min. After amplification, 5 µL of each sample or a BioMarker Low (BioVentures, Inc., Murfreeboro, Tenn.) DNA size standard were mixed with 1 µL of 6X loading dye and electrophoresed on a 3% Nusieve 3:1 agarose gel (FMC Bioproducts). The gel was stained in a 0.5 µg/mL ethidium bromide solution for 30 min and observed for the presence of amplification products under ultraviolet illumination.

Oligonucleotide DNA Probes
3) BPA/Neospora Internal Probe Sequence
 (5'-AGTCAAACGCG-3'(SEQ ID NO 7))
4) Toxoplasma Internal Probe Sequence
 (5'-AAGTCAACGCG-3'(SEQ ID NO 8))

Amplification products were denatured in the gel and transferred to nylon membranes (Hybond-N; Amersham Corp., Arlington Heights, Ill.) by the Southern blotting method. DNA was cross-linked to nylon membrane using a Stratalinker UV crosslinker (Stratagene, La Jolla, Calif.). Prehybridization, preparation of the labeled internal probe, and hybridization were performed as recommended by the manufacturer for the Enhanced Chemiluminescence 3'-oligolabeling and Detection Systems (Amersham). Labeled internal probe was added to a final concentration of 10 ng/mL of hybridization solution and incubated overnight at 30° C. with gentle agitation. After hybridization, the membranes were washed twice for 5 min each at room temperature in 5×SSC and 0.1% (w/v) SDS, and then washed twice for 5 min each at room temperature in 0.5× SSC and 0.1% (w/v) SDS. Membrane blocking, antibody incubations, signal generation and detection were performed as described by the manufacturer. Membranes were exposed to Kodak X-OMAT film for 3–10 min.

Results

Using the Neospora-specific primers 294 bp PCR products were amplified from DNAs of BPA-1 and Toxoplasma (RH and BT isolates). In addition, a 350 bp product was amplified from Sarcocystis cruzi DNA. No products were produced with DNAs from various bacteria, CPAE cells, and bovine thymocytes. Only the Neospora-specific probe hybridized to the Neospora amplification product. Similarly, the Toxoplasma-specific hybridized only to the Toxoplasma amplification product.

Example 5

This example describes experimental infections of pregnant cows with culture-derived Neospora tachyzoites.

Three cows were inoculated with $8 \times 10^6$ tachyzoites of the BPA1 Neospora isolate ($3 \times 10^6$ tachyzoites IV, and $5 \times 10^6$ tachyzoites IM). These cows were inoculated at 95 days gestation (Cow #412), 100 days gestation (Cow #416), and 105 days gestation (Cow #413). In each case, a Neospora fetal infection was confirmed (Cow #412 expelled an infected mummified fetus; Cow #416 gave birth to a calf that was in utero exposed; and an infected fetus was removed surgically from Cow #416). Two control cows were inoculated with uninfected cell culture and gave birth to uninfected live calves.

These cows were kept and rebred without any intervention. All three experimental cows gave birth to seronegative, clinically normal calves (not all post mortem tissues examined to date).

The cows were kept and rebred once again. The previously infected cows, 412, 416, 413, were then rechallenged by giving them the same inoculum ($8\times10^6$ tachyzoites, divided and given IV and IM) at 89, 83, and 83 days gestation, respectively. Control cows were rebred and observed. Two infected cows (413 and 416) gave birth to live calves which were clinically normal and seronegative to Neospora antigens. The third cow (#412) aborted 27 days post inoculation. The fetus was recovered. Although mild lesions suggestive of Neospora infection were found, Neospora infection, to date, has not been confirmed (formalin-fixed paraffin embedded tissues negative by immunohistochemistry). The cow was rebred and resorbed its fetus. She was rebred again and she aborted once again at 97 days gestation. This second fetus was not recovered. Thus far histopathologic examination or the tissues from the two clinically normal calves indicates that they were not tranplacentally infected with Neospora parasites.

This is the first experiment to show that cattle can be protected against Neospora abortion by immunization with culture-derived tachyzoites of the BPA-1 Neospora isolate.

Example 6

This example describes identification of two clones from Neospora cDNA library. These cDNAs can be used to produce recombinant immunodominant proteins useful for vaccines and immunodiagnostics.

METHODS AND METHODS

In vitro Cultivation

Neospora tachyzoites (BPA-1 isolate) and *Toxoplasma gondii* (RH strain) tachyzoites were cultivated in tissue culture as described in Conrad, *Parasitology*, 106:239–249 (1993). Briefly, BPA-1 tachzoites were grown in confluent layers of BAE (bovine aortic endothelial) cells, harvested and filtered through 5 μm disc filters to remove cellular debris, washed twice in phosphate buffered saline (PBS), and pelleted for use. After mRNA for cDNA library construction, BPA-1 and Toxoplasma tachyzoites were subsequently grown in Vero cells.

Isolation of Nucleic Acids

Total RNA was isolated from pelleted tissue culture cells with TRISOLV∂ reagent (Biofecx Laboratories, Houston, Tex.). Poly A+ RNA was selected by oligo (dT)-cellulose chromatography (Avis, el al., *Proc. Natl. Acad. Sci. USA* 69:1408–1412 (1972)). Integrity of RNA was monitored by electrophoresis on a formaldehyde gel and visualized with ethidium bromide using standard methods.

DNA was prepared with the IsoQuick NDA Extraction Kit (Microprobe Corp., Garden Grove, Calif.).

Construction of a Bovine Neospora cDNA Library in lgt11

Construction of a Neospora cDNA expression library in the vector λgt11 was performed essentially according to the manufacturer's protocol in the cDNA Synthesis Kit (Stratagene, La Jolla, Calif.). In short, first strand cDNA was synthesized from 5 μg of tachyzoitic poly(A) RNA using StrataScript RNase H reverse transcriptase and the second strand was synthesized with *E. coli* DNA polymerase. Subsequently, the double stranded cDNA was blunt-ended with the Klenow fragment, ligated to Eco R1 adaptors on both ends, kinased with T4 polynucleotide, and size-fractionated on a Sephacryl S-400 spin column. The final cDNA product was then ligated into the Eco R1 digested and dephosphorylated λgt11 vector and packaged using the Gigapack III Gold Packaging Extract (Stratagene, La Jolla, Calif.). The library contained $7\times10^6$ phages with approximately 97% of these being recombinants. Subsequently, one round of library amplification was completed in *E. coli* Y1088.

The Immunoscreening of the cDNA Library

The library was plated on *E. coli* Y1090r- and duplicate nitrocellulose plate lifts were screened with high titer sera from naturally infected cow D91-4696 and experimentally infected cow #416 described in Conrad, et al., *J. Vet. Diagn. Invest.*, 5:572–578 (1993). Sera were first pre-absorbed with Y1090r-bacterial lysates and then diluted 1:300 in TBS-T (10 mM Tris-HCl pH 8, 150 mM NaCl, 0.05% Tween 20) containing 5% horse serum and used for screening. Bound antibodies were visualized with alkaline phosphatase conjugated goat anti-bovine IgG diluted 1:5000 in TBS-T, 5% HS. Immunoscreening procedure was essentially as described for immunoblot assays below except 5% nonfat dry milk was replaced with 5% horse serum.

DNA Sequencing

PCR products generated with universal λgt11 primers flanking the vector's Eco R1 restriction site (Promega, Madison, Wis.) were used as templates for sequencing. Cycling conditions were as described by Obar, et al., *Methods in Cell Biology*, 37:361–406 (1993). Two sets of templates for sequencing were made for each clone and both were sequenced in the forward and reverse directions.

Automated DNA sequencing was accomplished with the ABI 373 DNA Sequencer and the DNA Sequencing Kit with AmphiTaq Polymerase FS (Perkin-Elmer Corp., Foster City, Calif.). Dye terminator chemistry in conjunction with cycle sequencing was used.

Southern and Northern Blot Analysis

For Southern blotting, 4 μg of genomic DNA was digested with restriction enzyme and separated on a 0.8% agarose gel according to standard procedures. After the gel was depurinated with 250 mM HCl for 10 minutes, denatured with 1.5 M NaCl, 0.5 M Tris-HCl, pH 7.5 for 30 minutes, the nucleic acids were transferred overnight to Hybond-N nylon membranes (Amersham Corp., Arlington Heights, Ill.) and crosslinked to the membrane via a UV crosslinker (Stratagene, La Jolla, Calif.). For probes, Eco R1 inserts from the recombinant clones were labeled with the ECI Direct Nucleic Acid Labeling and Detection Systems (Amersham Corp.). Blots were prehybridized with the ECL Gold Hybridization buffer containing 5% blocking agent and 0.5 M NaCl (Amersham Corp.) for 1 hour and hybridized with the probes overnight at 42° C. The blots were washed at 42° C. (2×20 min.) in 6M Urea, 0.4% SDS, 0.5×SSC and rinsed with 20×SSC prior to autoradiography.

For northern blotting, the above Southern blot procedure was essentially followed except that 0.4 μg mRNA (clone N54) or 5 μg of total RNA (clone N57) were run on a 1% formaldehyde gel and no extensive treatment of the gel was required prior to transfer. Also, when the Eco R1 insert from clone N54 was used as a probe, the wash protocol was adjusted to 0.4% SDS, 0.5×SSC at 45EC (2×20 min.).

Recombinant Protein Expression and Purification

To construct the expression vector, PCR products of the clone inserts were digested with Eco R1 and gel purified. This DNA was ligated into the Eco R1 digested and dephosphorylated pRSET B vector (Kroll, et al., *DNA and Cell Biology*, 12 441–453 (1993)) and the resulting plasmid was transformed into BL21 DE3 pLysS *E. coli* (Studier, et al., *Methods Enzynol.* 185:60–89 (1990)). Fusion proteins expressed from this plasmid contained a hexamer of histidines which allowed purification through a $Ni^{2+}$ affinity column under denaturing conditions.

Single colonies with high expression levels were inoculated into Luria Broth containing 100 μg/mL ampicillin and grown at 37° C. to an O.D.$_{.600}$ of 0.6. Overexpression of fusion proteins was initiated with the addition of isopropyl-P, D-thiogalactopyranoside (0.4 mM final) and shaking for 3 hours. Affinity column purification with a nickel-NTA-agarose affinity (Qiagen, Chetsworth, Calif.) under denaturing conditions was completed as described by Kroll, et al., *DNA and Cell Biology* 12 441–453 (1993). Samples were concentrated with a Centricon-10 (Amicon, Beverly, Mass.) and further purified by (size chromatography) with Sephadex G-150 superfine (Pharmacia, Uppsala, Sweden) equilibrated in 8 M urea, 0.1 M $Na^+$ phosphate, 0.01 M Tris, pH 4.5 using standard methods. Denaturants in the final proteins were removed by a slow 1 M urea stepwise dialysis to a final PBS, pH 7.4 buffer. Samples were concentrated again with Centricon-10 (Amicon,. Beverly, Mass.) and quantitated with the BCA Protein Assay (Pierce, Rockford, Ill.).

Polyclonal Antibody Production

Female New Zealand White rabbits were immunized subcutaneously with 400 μg of recombinant proteins in a 50% emulsion of Freund's complete adjuvant and thereafter boosted twice at 4 week intervals with 200 μg and then 100 μg of protein in incomplete Freund's adjuvant. Sera were obtained two weeks after the third immunization and used for immunoblots.

Immunoblots

Proteins were analyzed on a 12% polyacrylamide gel or a 4–20% gradient slab gel (Anderson, et al. *J. Am. Vet. Med. Assoc.*, 207:1206–1210 (1995)). Parasite antigens were harvested from tissue culture as described above, washed 2× in PBS, lysed with water, freeze thawed 3×, and sonicated. Both recombinant antigens and parasite antigens were quantitated with the BCA Protein Assay (Pierce), denatured in Laemmli's sample buffer and boiled for 5 minutes prior to electrophoresis. SDS-PAGE and Western blots were performed under standard conditions.

Rabbit antisera to the recombinant antigens, Neospora (BPA1) (Conrad, *Parasitology*, 106:239–249 (1993)), and *Toxoplasma gondii* (Conrad, *Parasitology*, 106:239–249 (1993)) were diluted 1:300 in TBS-Tween, 5% Blotto and incubated for 5 hours at room temperature. The secondary antibody, HRP-goat anti-rabbit (Jackson Laboratories) was diluted 1:1000 in the same buffer and incubated for 2 hours at room temperature. Blots were developed with 4-chloronaphthol and $H_2O_2$.

RESULTS

After one round of amplification, a bovine Neospora λgt11 cDNA library was generated containing $5.3 \times 10^{10}$ pfu/mL. Sera from cow D91-4696 and cow 416 which had high titers to Neospora antigens were chosen to screen the library. No significant banding pattern differences were seen between wstern blots which were incubated with these sera (data not shown). Both naturally infected cow D91-4696 and experimentally infected cow 416 tested negative for Toxoplasma gondii. Experimentally infected cow 416 was a subject of a previous Neospora abortion study (Conrad, et al., *J. Vet. Diagn. Invest.* 5:572–578 (1993)).

Primary screening of 200,000 cDNA clones with the above sera identified 61 double positive clones. Two were further characterized and designated N54 and N57. Based on agarose gel electrophoresis, the λgt11 Eco R1 inserts were 430 and 630 base pairs respectively.

Sequence analysis of clone N54 revealed that the cDNA insert was 407 bases within an open reading frame. The clone was not full length as indicated by the absence of a 5'-methione start site and the absence of a 3' stop codon and poly A tail (SEQ ID NO 9). Translation of the sequence into its corresponding amino acids revealed that the protein sequence was highly proline rich (32%) and composed of several repeat units (SEQ ID NO 10). Of particular interest is the sequence, SPPQS(S/Y)PPEP shown in bold in FIG. 5A, which occurs twice and has a high surface probability (Emini ave. index=3.025) and moderate antigenicity index (Jameson-Wolf ave. index=1.24). Other unique repeats within the region are the tetrapeptides, HP(H/P)P and SPP (E/Q), which occur four times each within the 135 amino acid sequence and the sequence, SY(A/P)P(D/E)PSP, which contains conserved substitutions.

Unlike clone N54, clone N57 contained a 3' stop codon and a long poly A tail (SEQ ID NO 11); however, because of difficulties in sequencing the repetitive noncoding region, only the coding sequences are shown (SEQ ID NO 12). While this partial clone did not have any discernible peptide repeats within its 76 amino acid sequence, upon inspection at the DNA level, multiple units of nucleotide repeats were identified. In particular, a long tandem repeat with 74% homology was present at the 3' end (FIG. 5B). While these repeats were similar at the nucleotide level, the multiple deletions within the repeats resulted in frame shifts that translated into peptide sequences with only 2 out of 10 amino acids being similar. By Emini analysis, these two regions appeared to be likely surface exposed and a correlation between surface exposure and antigenicity was seen. The second repeat also appeared to have a potential glycosylation at the position 50 asparagine. In addition, there was a high frequency of nine GGA(A/G) repeats clustered within a 105 base region at the 3' end of the gene sequence.

Clones N54 and N57 hybridized to bands of different molecular weights on Southern blots of Neospora (BPA-1) DNA, indicating that the clones were derived from separate Neospora genes. Clone N54 showed some hybridization to a higher molecular weight band of *Toxoplasma gondii* DNA, whereas clone N57 did not bind to Toxoplasma DNA or to Vero DNA.

Northern blots with the same probes also showed that both clones recognized different molecular weight RNA transcripts and thus, encoded distinct Neospora proteins. Clone N54 bound to a 4.2 kb Neospora transcript, while clone N57 bound to a shorter 1.4 kb transcript. Neither clones hybridized to *Toxoplasma gondii* RNA or Vero RNA.

When clones N54 and N57 were expressed as histidine fusion proteins from the pRSET vectors, the resulting protein product of clone N54 was 29.3 kD whereas the protein product of clone N57 was 20.1 kD. By Western blot analysis, both proteins were recognized by rabbit antisera to BPA1 and not by rabbit *Toxoplasma gondii* antisera (data not shown). This suggests that the recombinant antigens are more diagnostically useful than the whole lysate which did have some reactivity to rabbit *Toxoplasma gondii* antisera.

In addition, polyclonal monospecific antisera to clones N54 and N57 only bound to Neospora antigens on reducing and nonreducing western blots. Rabbit anti-N54 recognized Neospora bands of molecular weights 97.2 kD, 87.9 kD, 77.1 kD, 67.4 kD, 64.3 kD, 60.1 kD, 55.3 kD, and 28.3–28 (reducing) and 126.7 kD, 89.4 kD, 68.7 kD, 58.4 kD, 55.2 kD, 54.5 kD, 52.7 kD, 49.7 kD, 46.7 kD and 26.5–27.9 (nonreducing). Rabbit anti-N57 recognized Neospora bands to molecular weights 33.6 kD, 31.4 kD, 27.5 kD, and 22.4 kD (reducing) and 32.8 kD, 30.6 kD, 28.4 kD, 26.3 kD, and 21.0 kD (nonreducing). Neither polyclonal antisera bound to *Toxoplasma gondii* antigens nor to Vero cell antigens, making these two recombinant antigens promising candidates for a highly specific ELISA.

CONCLUSION

Current ELISA protocols require the use of in vitro cultivated of Neospora tachyzoites for coating antigens. (Pare, et al., *J. Vet. Diag. Invest.*, 7:352–9 (1995); Bjorkman, et al., *Parasite Immunology*, 16:643–8). When using such a crude mixture of antigens, one runs the risk of generating false positives due to crossreactivity between proteins from closely related parasites. By using one or two Neospora specific recombinant antigens in an ELISA, potentially crossreactive antigens are removed. In addition, the use of whole parasites requires time consuming and expensive tissue culture methods.

Example 7

This example discloses the cloning of the full-length cDNA, known as NC-p65, that includes the N54 fragment.

Neospora (BPA-1 isolate) tachyzoites were grown in tissue culture as previously described, except that tachyzoites were grown on Vero cells. (Conrad, et al., *Parasitology* 106:239 (1993)). Briefly, for purification of the parasites, tachyzoites and Vero cells were scraped off the tissue culture flask, centrifuged, resuspended in 3 mL of phosphate buffered saline (PBS), passed three times through a 22-gauge needle to release the tachyzoites from the feeder cells, and passed through a PD-10 column filled with PBS-equilibrated Sephadex G25M (Pharmacia). The eluted tachyzoites were collected, centrifuged, and stored as a pellet at $-70°$ C. Uninfected Vero cells for use as negative control material were also scraped, centrifuged, and stored as a pellet at $-70°$ C.

Total RNA was isolated from pelleted tissue culture parasites with TRJSOLV reagent (Biotecx Laboratories, Inc.). Poly(A) RNA was selected by oligo(dT)-cellulose chromatography (Avis & Leder, *Proc. Nat'l Acad. Sci. USA* 69:1408 (1972)). Construction of a cDNA library with Marathon adaptor-ligated ends was completed using the Marathon™ cDNA Amplification Kit (Clonetech Laboratories, Inc.). Five' and 3'-rapid amplification of cDNA ends (RACE) were performed using this library to obtain the sequence of the full length NC-p65 cDNA. Design of the gene specific primers for 5'-RACE and 3'-RACE was based on the sequence of N54 which was located internally in the NC-p65 cDNA. (Louie, et al., *Clin. Diagn. Lab. Immunol.* 4: 692 (1997)). The 3' gene-specific primer for 5'-RACE was a 27-mer with the base composition, 5'-GAGGCGAAGGGACTCTCGGAGAAGAAC-3' (SEQ ID NO: 20. The 5' gene-specific primer for 3'-RACE was a 26-mer with the sequence, 5'-GAACCTTCACCATCGAAGCCGTCTCC-3' (SEQ ID NO: 21). Following 5'-RACE with the 3' gene-specific primer and the Marathon adaptor primer (Clonetech Laboratories, Inc.) and 3'- RACE with the 5' gene-specific primer and the Marathon adaptor primer, two overlapping PCR products which represented the complete 5' end and the complete 3' end of the NC-p65 cDNA were generated. Nucleotide sequencing of these products was completed.

From the sequence information, the forward primer, 5'-TCAGCTCGAGCAACACGGTCACGGGAACAATGA G-3' (SEQ ID NO: 22), and the reverse primer, 5'-TGACGAATTCCCAGATGTGACGGGGACATCACYA C-3' (SEQ ID NO: 23), were designed and used to PCR a continuous clone representing the entire coding region of the NC-p65 cDNA. The reaction mixture contained 1.5 ng of the adaptor-ligated cDNA library, 0.4 mM of each primer, 0.2 mM dNTP, 1×KlenTaq buffer, and 1× Advantage Klentaq Polymerase Mix (Clontech Laboratories, Inc.). "Touchdown" PCR cycling conditions were 94° C. for 1 min; 5 cycles at 940 C for 30 sec and 72° C. for 4 min; 5 cycles at 94° C. for 30 sec and 70° C. for 4 min; and 25 cycles at 94° C. for 30 sec and 68° for 4 min.

The 5'- and 3'-RACE PCR products were inserted into plasmid vector, pCR 11, with the aid of the TA Cloning Kit (Invitrogen Corporation) and used as templates for sequencing. Both the forward and reverse directions were sequenced by fluorescent dye termination thermal cycling and analyzed on the ABI 377 automated sequencer (Advanced Biosystems) as previously described (Louie, et al. *Clin. Diagn. Lab. Immunol.* 4:692 (1997)). The full length sequence is as shown in SEQ ID NO: 18. Protein sequence analysis was performed using the Genetics Computer Group (GCG) programs, BLASTP, FASTA, Motifs, Bestfit, and Gap. The deduced amino acid sequence is as shown in SEQ ID NO: 19.

NC-p65 is a serine protease located in the microneme organelles of the parasite and is released into culture supernatant during periods of visible host cell invasion. Unlike all other Apicomplexan microneme proteins, NC-p65 is the first identified microneme protein to have a described activity other than host cell attachment. It is also the first to have a demonstrated proteolytic activity and illustrates a new, alternative function for the proteins of the microneme organelle. Because of its location in a secretory organelle and in the supernatant, and because of its proven enzymatic activity, it is likely that NC-p65 is involved in aiding host cell invasion.

Example 8

Future research to elucidate the role and importance of NC-p65 in parasite development will gain insights on how to better control Neospora infections. These experiments can include "knock out" parasites and substrate binding studies.

By "knocking out" the NC-p65 gene, it can be determined if the proteolytic activity is essential for growth. By studying the substrate, those of skill will learn when, where, and why the enzyme acts.

The technology to create a "knock out" parasite with a deleted gene is available for Apicomplexan parasites and several "knock outs" of malaria and toxoplasma parasites have already been generated. For production of a NC-p65 "knock out" in *Neospora caninum*, upstream and downstream sequences of the NC-p65 are identified for use as sites for homologous recombination (in addition to primers for sequencing or probes for hybridization). A construct for specific homologous recombination is generated and genetic replacement of the NC-p65 gene with a reporter gene, for example, chloramphenicol acetyltransferase (CAT), can be created. Genetically engineered parasites are isolated by chloramphenicol selection, tested for successful homologous recombination by Southern and western blots.

If NC-p65 performs a key function, a genetic "knock out" of NC-p65 will likely produce a non-viable recombinant parasite. NC-p65 can become a major target for drug discovery research and lead the way to the development of novel class of drugs. These new chemical compounds can be identified by their abilities to inhibit the proteolytic activity of NC-p65 and arrest the development of the parasite.

To identify the substrate of this protease, native, active NC-p65 is purified from Neospora tachyzoite lysates or from the supernatant. Once a purified enzyme is in hand, the substrate can be identified. Most directly, the enzyme can be coupled onto a resin and used as an affinity resin to purify the ligand/substrate. Alternatively, substrates of host cell or parasitic origin can be radiolabeled and treated with the purified NC-p65. Comparison of the pre- and post-treated samples by electrophoresis would reveal a change in protein pattern and, at minimum, reveal the source of the substrate.

Based on the knowledge gained from the substrate studies, these drug candidates are chemically modified to increase their binding to the enzyme and, therefore, become effective competitors with the natural substrate.

The above examples are provided to illustrate the invention but not to limit its scope. Other variants of the invention will be readily apparent to one of ordinary skill in the art and are encompassed by the appended claims. All publications, patents, and patent applications cited herein are hereby incorporated by reference.

What is claimed is:

1. A method for obtaining a normal calf from a bovine animal, comprising the steps of:
   (i) administering to the bovine animal a pharmaceutical composition comprising a pharmaceutically acceptable carrier and an immunogenically effective amount of a bovine Neospora tachyzoite;
   (ii) breeding the bovine animal; and
   (iii) obtaining a normal calf from the bovine animal.

2. The method of claim 1, wherein the bovine animal is a cow or heifer.

3. The method of claim 1, wherein the pharmaceutical composition is administered parenterally.

4. The method of claim 1, wherein the isolated bovine Neospora tachyzoite is attenuated.

5. The method of claim 1, wherein the bovine Neospora tachyzoite is selected from the group consisting of ATCC Accession No. 75710 (BPA1) and ATCC Accession No. 75711 (BPA6).

6. A method for protecting a bovine animal from Neospora abortion, the method comprising the administration of a pharmaceutical composition comprising a pharmaceutically acceptable carrier and an immunogenically effective amount of a bovine Neospora antigen, whereby the bovine animal is protected from abortion induced by Neospora infection, wherein the bovine Neospora antigen is an isolated bovine Neospora tachyzoite of ATCC Accession No. 75710 (BPA1) or ATCC Accession No. 75711 (BPA6).

7. The method of claim 6, wherein the bovine animal is a cow or heifer.

8. The method of claim 6, wherein the pharmaceutical composition is administered to the bovine animal prior to breeding.

9. The method of claim 6, wherein the isolated bovine Neospora tachyzoite is attenuated.

10. The method of claim 6, wherein the pharmaceutical composition is administered parenterally.

11. A method for protecting a bovine animal from Neospora abortion, the method comprising the administration of a pharmaceutical composition comprising a pharmaceutically acceptable carrier and an immunogenically effective amount of an isolated bovine Neospora tachyzoite that is attenuated, whereby the bovine animal is protected from abortion induced by Neospora infection.

12. The method of claim 11, wherein the bovine animal is a cow or heifer.

13. The method of claim 11, wherein the pharmaceutical composition is administered to the bovine animal prior to breeding.

14. The method of claim 11, wherein the pharmaceutical composition is administered parenterally.

15. The method of claim 11, wherein the bovine Neospora tachyzoite is selected from the group consisting of ATCC Accession No. 75710 (BPA1) and ATCC Accession No. 75711 (BPA6).

* * * * *

SEQUENCE LISTING

<160> NUMBER OF SEQ ID NOS: 23

<210> SEQ ID NO 1
<211> LENGTH: 1747
<212> TYPE: DNA
<213> ORGANISM: Neospora sp.
<220> FEATURE:
<223> OTHER INFORMATION: nuclear small subunit (nss)-rRNA gene

<400> SEQUENCE: 1

```
agtcatatgc ttgtcttaaa gattaagcca tgcatgtcta agtataagct tttatacggc     60
taaactgcga atggctcatt aaaacagtta tagtttattt gatggtcttt actacatgga    120
taaccgtggt aattctatgg ctaatacatg cgcacatgcc tcttcctctg gaagggcagt    180
gtttattaga tacagaacca acccaccttc cggtggtcct cgggtgattc atagtaaccg    240
aacggatcgc gtttgacttc ggtctgcgac ggatcattca agtttctgac ctatcagctt    300
tcgacggtac tgtattggac taccgtggca gtgacgggta acggggaatt agggttcgat    360
tccggagagg gagcctgaga aacggctacc acatctaagg aaggcagcag gcgcgcaaat    420
tacccaatcc tgattcaggg aggtagtgac aagaaataac aacactggaa atttcatttc    480
tagtgattgg aatgataggA atccaaaccc ctttcagagt aacaattgga gggcaagtct    540
ggtgccagca gccgcggtaa ttccagctcc aatagcgtat attaaagttg ttgcagttaa    600
aaagctcgta gttggatttc tgctggaagc agccagtccg ccctcagggg tgtgcacttg    660
gtgaattcta gcatccttct ggatttcttc acacttcatt gtgtggagtt ttttccagga    720
cttttacttt gagaaaatta gagtgtttca agcaggcttg tcgccttgaa tactgcagca    780
tggaataata agataggatt tcggccctat tttgttggtt tctaggactg aagtaatgat    840
taatagggac ggttggggc attcgtattt aactgtcaga ggtgaaattc ttagatttgt     900
taaagacgaa ctactgcgaa agcatttgcc aaagatgttt tcattaatca agaacgaaag    960 ttagggctc gaagacgatc agataccgtc gtagtcttaa ccataaacta tgccgactag    1020
agataggaaa acgtcatgct tgacttctcc tgcaccttat gagaaatcaa agtctttggg    1080
ttctgggggg agtatggtcg caaggctgaa acttaaagga attgacggaa gggcaccacc    1140
aggcgtggag cctgcggctt aatttgactc aacacgggga aactcaccag gtccagacat    1200
aggaaggatt gacagattga tagctctttc ttgattctat gggtggtggt gcatggccgt    1260
tcttagttgg tggagtgatt tgtctggtta attccgttaa cgaacgagac cttaacctgc    1320
```

```
taaataggat caggaacttc gtgttcttgt atcacttctt agagggactt tgcgtgtcta      1380
acgcaaggaa gtttgaggca ataacaggtc tgtgatgccc ttagatgttc tgggctgcac      1440
gcgcgctaca ctgatgcatc caacgagttt ataaccttgg ccgataggtc taggtaatct      1500
tgtgagtatg catcgtgatg gggatagatt attgcaatta ttaatcttca acgaggaatg      1560
cctagtaggc gcaagtcagc agcttgcgcc gattacgtcc ctgcccttg tacacaccgc       1620 ccgtcgctcc taccgattga gtgttccggt gaattattcg gaccgttttg tggcgcgttc      1680
gtgcccgaaa tgggaagttt tgtgaacctt aacacttaga ggaaggagaa gtcgtaacaa      1740
ggtttcc                                                                1747

<210> SEQ ID NO 2
<211> LENGTH: 52
<212> TYPE: DNA
<213> ORGANISM: Artificial Sequence
<220> FEATURE:
<223> OTHER INFORMATION: Description of Artificial Sequence:universal
      primer A

<400> SEQUENCE: 2
ccgaattcgt cgacacctgg ttgatccccg acgaccgtgg tctgaacggg ag              52

<210> SEQ ID NO 3
<211> LENGTH: 40
<212> TYPE: DNA
<213> ORGANISM: Artificial Sequence
<220> FEATURE:
<223> OTHER INFORMATION: Description of Artificial Sequence:primer C

<400> SEQUENCE: 3
gggccctagg tggcgccgac gaccgtggtc tgaacgggag                            40

<210> SEQ ID NO 4
<211> LENGTH: 39
<212> TYPE: DNA
<213> ORGANISM: Artificial Sequence
<220> FEATURE:
<223> OTHER INFORMATION: Description of Artificial Sequence:primer B

<400> SEQUENCE: 4
cccgggatcc aagcttgatc cttctgcagg ttcacctac                             39

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence:bovine
      Neospora forward PCR primer

<400> SEQUENCE: 5
aagtataagc ttttatacgg ct                                               22

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence:bovine
      Neospora reverse PCR primer

<400> SEQUENCE: 6
cactgccacg gtagtccaat ac                                               22
```

<210> SEQ ID NO 7
<211> LENGTH: 11
<212> TYPE: DNA
<213> ORGANISM: Artificial Sequence
<220> FEATURE:
<223> OTHER INFORMATION: Description of Artificial Sequence:BPA/Neospora internal probe sequence

<400> SEQUENCE: 7
agtcaaacgc g    11

<210> SEQ ID NO 8
<211> LENGTH: 11
<212> TYPE: DNA
<213> ORGANISM: Artificial Sequence
<220> FEATURE:
<223> OTHER INFORMATION: Description of Artificial Sequence:Toxoplasma internal probe sequence

<400> SEQUENCE: 8
aagtcaacgc g    11

<210> SEQ ID NO 9
<211> LENGTH: 407
<212> TYPE: DNA
<213> ORGANISM: Neospora sp.
<220> FEATURE:
<221> NAME/KEY: CDS
<222> LOCATION: (2)..(406)
<223> OTHER INFORMATION: clone N54 cDNA insert

<400> SEQUENCE: 9

```
g caa cat cct cat cct cat cct cct cgc cct aat ccc ccc gag gct tca      49
  Gln His Pro His Pro His Pro Pro Arg Pro Asn Pro Pro Glu Ala Ser
  1               5                  10                  15 cct ccg cag tcg tct ccg ccc gaa cct caa cgt cct ttt tct cag tgg        97
Pro Pro Gln Ser Ser Pro Pro Glu Pro Gln Arg Pro Phe Ser Gln Trp
             20                  25                  30 ccc cac act cca cat ttt ttt cat tat cat ccc tac cct gga tat aat       145
Pro His Thr Pro His Phe Phe His Tyr His Pro Tyr Pro Gly Tyr Asn
         35                  40                  45 ctt cct tat ttt act tac cat cag tct cct ctt cct tat ggt ccc tac       193
Leu Pro Tyr Phe Thr Tyr His Gln Ser Pro Leu Pro Tyr Gly Pro Tyr
     50                  55                  60 gga agg gat cct tgt cct tgt gct tcc cac cct tat ccc gcc gac gat       241
Gly Arg Asp Pro Cys Pro Cys Ala Ser His Pro Tyr Pro Ala Asp Asp
 65                  70                  75                  80 tca cct ctg ggg tcg tat gcg ccc gat cca tca cct ccc cag tct tat       289
Ser Pro Leu Gly Ser Tyr Ala Pro Asp Pro Ser Pro Pro Gln Ser Tyr
                 85                  90                  95 ccc cca gaa cct tca cca tcg aag ccg tct cca cca gag ggt tct tct       337
Pro Pro Glu Pro Ser Pro Ser Lys Pro Ser Pro Pro Glu Gly Ser Ser
            100                 105                 110 ccg aga gtc cct tcg cct cac cgg cat ccc agc aga tca cgt ctc ccc       385
Pro Arg Val Pro Ser Pro His Arg His Pro Ser Arg Ser Arg Leu Pro
        115                 120                 125 tct gct gtc gag cca tct cca c                                          407
Ser Ala Val Glu Pro Ser Pro
    130                 135
```

<210> SEQ ID NO 10
<211> LENGTH: 135
<212> TYPE: PRT

<213> ORGANISM: Neospora sp.
<223> OTHER INFORMATION: clone N54 cDNA insert

<400> SEQUENCE: 10

Gln His Pro His Pro His Pro Arg Pro Asn Pro Pro Glu Ala Ser
1               5                   10                  15

Pro Pro Gln Ser Ser Pro Pro Glu Pro Gln Arg Pro Phe Ser Gln Trp
            20                  25                  30

Pro His Thr Pro His Phe Phe His Tyr His Pro Tyr Pro Gly Tyr Asn
        35                  40                  45

Leu Pro Tyr Phe Thr Tyr His Gln Ser Pro Leu Pro Tyr Gly Pro Tyr
    50                  55                  60

Gly Arg Asp Pro Cys Pro Cys Ala Ser His Pro Tyr Pro Ala Asp Asp
65              70                  75                  80

Ser Pro Leu Gly Ser Tyr Ala Pro Asp Pro Ser Pro Gln Ser Tyr
            85                  90                  95

Pro Pro Glu Pro Ser Pro Ser Lys Pro Ser Pro Glu Gly Ser Ser
            100                 105                 110

Pro Arg Val Pro Ser Pro His Arg His Pro Ser Arg Ser Arg Leu Pro
            115                 120                 125

Ser Ala Val Glu Pro Ser Pro
        130             135

<210> SEQ ID NO 11
<211> LENGTH: 232
<212> TYPE: DNA
<213> ORGANISM: Neospora sp.
<220> FEATURE:
<221> NAME/KEY: CDS
<222> LOCATION: (2)..(232)
<223> OTHER INFORMATION: clone N57 cDNA insert

<400> SEQUENCE: 11 c ata gcc gcg tta gtt gca gca gcc gca ttt gct gga ttg ggt ctc gcg      49
  Ile Ala Ala Leu Val Ala Ala Ala Ala Phe Ala Gly Leu Gly Leu Ala
  1               5                   10                  15 aga aca ttc agg cat ttc gtg cca aaa aag tca aag acg gtt gcg agt        97
Arg Thr Phe Arg His Phe Val Pro Lys Lys Ser Lys Thr Val Ala Ser
            20                  25                  30 gag gac tct gcg ctc gga aac agt gaa gag cag tat gtg gaa gga acc        145
Glu Asp Ser Ala Leu Gly Asn Ser Glu Glu Gln Tyr Val Glu Gly Thr
        35                  40                  45 gtg aac ggg agc agt gat ccg gaa cag gag cgg gcg ggt ggg cct ctt        193
Val Asn Gly Ser Ser Asp Pro Glu Gln Glu Arg Ala Gly Gly Pro Leu
    50                  55                  60 atc ccg gaa gga gac gag cag gaa gta gac acc gaa tag                    232
Ile Pro Glu Gly Asp Glu Gln Glu Val Asp Thr Glu
65              70                  75

<210> SEQ ID NO 12
<211> LENGTH: 76
<212> TYPE: PRT
<213> ORGANISM: Neospora sp.
<223> OTHER INFORMATION: clone N57 cDNA insert

<400> SEQUENCE: 12

Ile Ala Ala Leu Val Ala Ala Ala Ala Phe Ala Gly Leu Gly Leu Ala
1               5                   10                  15

Arg Thr Phe Arg His Phe Val Pro Lys Lys Ser Lys Thr Val Ala Ser
            20                  25                  30

Glu Asp Ser Ala Leu Gly Asn Ser Glu Glu Gln Tyr Val Glu Gly Thr
            35                  40                  45

Val Asn Gly Ser Ser Asp Pro Glu Gln Glu Arg Ala Gly Gly Pro Leu
    50                  55                  60

Ile Pro Glu Gly Asp Glu Gln Glu Val Asp Thr Glu
 65                 70                  75

<210> SEQ ID NO 13
<211> LENGTH: 10
<212> TYPE: PRT
<213> ORGANISM: Artificial Sequence
<220> FEATURE:
<223> OTHER INFORMATION: Description of Artificial Sequence:peptide
      repeat unit
<220> FEATURE:
<221> NAME/KEY: MOD_RES
<222> LOCATION: (6)
<223> OTHER INFORMATION: Xaa = Ser or Tyr

<400> SEQUENCE: 13

Ser Pro Pro Gln Ser Xaa Pro Pro Glu Pro
 1               5                   10

<210> SEQ ID NO 14
<211> LENGTH: 4
<212> TYPE: PRT
<213> ORGANISM: Artificial Sequence
<220> FEATURE:
<223> OTHER INFORMATION: Description of Artificial Sequence:peptide
      repeat unit
<220> FEATURE:
<221> NAME/KEY: MOD_RES
<222> LOCATION: (3)
<223> OTHER INFORMATION: Xaa = His or Tyr

<400> SEQUENCE: 14

His Pro Xaa Pro
 1

<210> SEQ ID NO 15
<211> LENGTH: 4
<212> TYPE: PRT
<213> ORGANISM: Artificial Sequence
<220> FEATURE:
<223> OTHER INFORMATION: Description of Artificial Sequence:peptide
      repeat unit

<400> SEQUENCE: 15

Ser Pro Pro Glx
 1

<210> SEQ ID NO 16
<211> LENGTH: 57
<212> TYPE: DNA
<213> ORGANISM: Neospora sp.
<220> FEATURE:
<221> NAME/KEY: repeat_region
<222> LOCATION: (1)..(57)
<223> OTHER INFORMATION: extended tandem DNA repeat within clone N57

<400> SEQUENCE: 16
ggaaacagtg aagagcagta tgtggaagga accgtgaacg ggagcagtga tccggaa        57

<210> SEQ ID NO 17
<211> LENGTH: 7
<212> TYPE: PRT
<213> ORGANISM: Artificial Sequence
<220> FEATURE:

-continued

```
<223> OTHER INFORMATION: Description of Artificial Sequence:peptide
      repeat unit
<220> FEATURE:
<221> NAME/KEY: MOD_RES
<222> LOCATION: (3)
<223> OTHER INFORMATION: Xaa = Ala or Pro
<220> FEATURE:
<221> NAME/KEY: MOD_RES
<222> LOCATION: (5)
<223> OTHER INFORMATION: Xaa = Asp or Glu

<400> SEQUENCE: 17

Ser Tyr Xaa Pro Xaa Pro Ser
  1               5

<210> SEQ ID NO 18
<211> LENGTH: 2595
<212> TYPE: DNA
<213> ORGANISM: Neospora sp.
<220> FEATURE:
<221> NAME/KEY: CDS
<222> LOCATION: ()..(2595)
<223> OTHER INFORMATION: NC-p65 cDNA

<400> SEQUENCE: 18
```

| | | | | | | | | | | | | | | | | |
|---|---|---|---|---|---|---|---|---|---|---|---|---|---|---|---|---|
| atg | agg | gcg | tcg | cat | atc | ctc | ctt | gcg | tgt | agt | gtc | ttg | atc | gtg | ttg | 48 |
| Met | Arg | Ala | Ser | His | Ile | Leu | Leu | Ala | Cys | Ser | Val | Leu | Ile | Val | Leu | |
| 1 | | | | 5 | | | | | 10 | | | | | 15 | | |
| tta | tgt | atg | gac | gcg | aga | gga | ctc | cgg | gtg | agg | aaa | gat | gga | gac | gta | 96 |
| Leu | Cys | Met | Asp | Ala | Arg | Gly | Leu | Arg | Val | Arg | Lys | Asp | Gly | Asp | Val | |
| | | | 20 | | | | | 25 | | | | | 30 | | | |
| cta | tcg | ccg | aag | act | ttc | cag | cct | gat | gga | ggg | gag | aat | acc | acg | gac | 144 |
| Leu | Ser | Pro | Lys | Thr | Phe | Gln | Pro | Asp | Gly | Gly | Glu | Asn | Thr | Thr | Asp | |
| | | 35 | | | | | 40 | | | | | 45 | | | | |
| cca | tct | gat | atc | atc | gaa | gag | gtc | cga | aag | gta | gaa | aaa | caa | gta | gaa | 192 |
| Pro | Ser | Asp | Ile | Ile | Glu | Glu | Val | Arg | Lys | Val | Glu | Lys | Gln | Val | Glu | |
| | 50 | | | | | 55 | | | | | 60 | | | | | |
| gct | gag | gcg | gca | gaa | ata | att | aaa | gcc | aga | gag | gag | cat | cgt | ggt | ttc | 240 |
| Ala | Glu | Ala | Ala | Glu | Ile | Ile | Lys | Ala | Arg | Glu | Glu | His | Arg | Gly | Phe | |
| 65 | | | | | 70 | | | | | 75 | | | | | 80 | |
| aac | aca | ctt | gac | gat | ggc | gtc | gcc | ccg | gag | aca | gag | ggt | ggg | cat | gga | 288 |
| Asn | Thr | Leu | Asp | Asp | Gly | Val | Ala | Pro | Glu | Thr | Glu | Gly | Gly | His | Gly | |
| | | | | 85 | | | | | 90 | | | | | 95 | | |
| ctg | cat | gct | tca | gag | acg | act | cct | gtt | gca | gag | ctc | gaa | cca | caa | gat | 336 |
| Leu | His | Ala | Ser | Glu | Thr | Thr | Pro | Val | Ala | Glu | Leu | Glu | Pro | Gln | Asp | |
| | | | | 100 | | | | | 105 | | | | | 110 | | |
| cca | gac | cgg | agt | ctc | aag | tat | cct | gta | cgg | ctg | ctg | att | gta | gac | aag | 384 |
| Pro | Asp | Arg | Ser | Leu | Lys | Tyr | Pro | Val | Arg | Leu | Leu | Ile | Val | Asp | Lys | |
| | | 115 | | | | | 120 | | | | | 125 | | | | |
| cct | gcg | ggg | gat | gaa | gag | gag | act | aga | cca | tca | ttt | gtg | cag | acg | gca | 432 |
| Pro | Ala | Gly | Asp | Glu | Glu | Glu | Thr | Arg | Pro | Ser | Phe | Val | Gln | Thr | Ala | |
| | 130 | | | | | 135 | | | | | 140 | | | | | |
| cta | cat | tcg | gag | ctt | gca | caa | cgc | gtt | gtg | aaa | gag | cta | aat | ggg | cat | 480 |
| Leu | His | Ser | Glu | Leu | Ala | Gln | Arg | Val | Val | Lys | Glu | Leu | Asn | Gly | His | |
| 145 | | | | | 150 | | | | | 155 | | | | | 160 | |
| gtg | gac | gtt | ctt | gat | gag | agc | ggc | gtg | gtc | cta | gtg | gat | ctt | cca | gca | 528 |
| Val | Asp | Val | Leu | Asp | Glu | Ser | Gly | Val | Val | Leu | Val | Asp | Leu | Pro | Ala | |
| | | | | 165 | | | | | 170 | | | | | 175 | | |
| aac | acc | acg | gac | aaa | caa | ctc | aag | gag | gtg | att | gaa | aca | gcc | aag | gcg | 576 |
| Asn | Thr | Thr | Asp | Lys | Gln | Leu | Lys | Glu | Val | Ile | Glu | Thr | Ala | Lys | Ala | |
| | | | | 180 | | | | | 185 | | | | | 190 | | |
| caa | ggc | gcc | ata | gta | gag | ccg | gac | cat | atg | gtc | agc | gct | gtc | cat | aca | 624 |
| Gln | Gly | Ala | Ile | Val | Glu | Pro | Asp | His | Met | Val | Ser | Ala | Val | His | Thr | |
| | | | 195 | | | | | 200 | | | | | 205 | | | |

```
tcg tcg aga gaa tca aat gac ccg ttg ctg cat gag ctc tgg gct ttg      672
Ser Ser Arg Glu Ser Asn Asp Pro Leu Leu His Glu Leu Trp Ala Leu
        210                 215                 220 gat ccg tta aac atg cga gcg gct tgg gac atc ttg acc aca gca gaa      720
Asp Pro Leu Asn Met Arg Ala Ala Trp Asp Ile Leu Thr Thr Ala Glu
225                 230                 235                 240 ctt ggc ggg gat cgg agg cca ctg gtc tgt gtt gta gat act ggc atc      768
Leu Gly Gly Asp Arg Arg Pro Leu Val Cys Val Val Asp Thr Gly Ile
                    245                 250                 255 gat tat gag cac ccg gac tta cgt gaa aac atg gaa gtg aac cag gta      816
Asp Tyr Glu His Pro Asp Leu Arg Glu Asn Met Glu Val Asn Gln Val
                260                 265                 270 gag ctg cac ggc aag ccc gga att gac gac gac aac aac ggg gag att      864
Glu Leu His Gly Lys Pro Gly Ile Asp Asp Asp Asn Asn Gly Glu Ile
            275                 280                 285 gac gac atc tac ggg gcc aac atg gtc agc gat tcc acc gac cct gcg      912
Asp Asp Ile Tyr Gly Ala Asn Met Val Ser Asp Ser Thr Asp Pro Ala
        290                 295                 300 gat gat cac tct cat ggc act cac gtg gcc gga acc att ggt gca cgg      960
Asp Asp His Ser His Gly Thr His Val Ala Gly Thr Ile Gly Ala Arg
305                 310                 315                 320 gga gac aat ggc gtc gga ata gct ggt att gca tgg gca ccc cgt ctc     1008
Gly Asp Asn Gly Val Gly Ile Ala Gly Ile Ala Trp Ala Pro Arg Leu
                    325                 330                 335 att gca tgc aaa ttc ttg aag ccc cga gga aga gga ttc gac tca gat     1056
Ile Ala Cys Lys Phe Leu Lys Pro Arg Gly Arg Gly Phe Asp Ser Asp
                340                 345                 350 gcg ctc cgt tgc att aac tat tgc gcc aaa aga ggc gcc gat att atg     1104
Ala Leu Arg Cys Ile Asn Tyr Cys Ala Lys Arg Gly Ala Asp Ile Met
            355                 360                 365 aac cat agt tgg agt ggt tca gat gca agt gaa gct ctt cgt caa gca     1152
Asn His Ser Trp Ser Gly Ser Asp Ala Ser Glu Ala Leu Arg Gln Ala
        370                 375                 380 atc gag caa acg gcg caa caa ggc atc att cac atc gcc gca gca gga     1200
Ile Glu Gln Thr Ala Gln Gln Gly Ile Ile His Ile Ala Ala Ala Gly
385                 390                 395                 400 aat tcc ggt aga gac gtc gac gtg acc cca aat tac cca gca gca tta     1248
Asn Ser Gly Arg Asp Val Asp Val Thr Pro Asn Tyr Pro Ala Ala Leu
                    405                 410                 415 tcg acg gct gtg gaa ggg ctc atc aca gtc gga aat atg aaa atg gaa     1296
Ser Thr Ala Val Glu Gly Leu Ile Thr Val Gly Asn Met Lys Met Glu
                420                 425                 430 aag cag cgc gac ggg tcg aag cat ttt tcc ttg gct gaa tcc agt aac     1344
Lys Gln Arg Asp Gly Ser Lys His Phe Ser Leu Ala Glu Ser Ser Asn
            435                 440                 445 tat gga acc aaa agc gtt cag att gcc ttg cca ggg acg gac atc tat     1392
Tyr Gly Thr Lys Ser Val Gln Ile Ala Leu Pro Gly Thr Asp Ile Tyr
        450                 455                 460 tct act att cct gtg caa gag cgc ccg gat gac ccc tat gga tgg aag     1440
Ser Thr Ile Pro Val Gln Glu Arg Pro Asp Asp Pro Tyr Gly Trp Lys
465                 470                 475                 480 aca ggg aca tca atg gca gct cct gct ctc agc gga atc gtt gct tta     1488
Thr Gly Thr Ser Met Ala Ala Pro Ala Leu Ser Gly Ile Val Ala Leu
                    485                 490                 495 atg ctc gcg gcg aat cct gga ctg agt gca acc caa atc aga tct att     1536
Met Leu Ala Ala Asn Pro Gly Leu Ser Ala Thr Gln Ile Arg Ser Ile
                500                 505                 510 tta atg caa agt gtg aac cgg acg cct gag ctc tca acc cga gtg aca     1584
Leu Met Gln Ser Val Asn Arg Thr Pro Glu Leu Ser Thr Arg Val Thr
```

-continued

|  |  |  |  |  |  |  |  |  |  |  |  |  |  |  |  |  |
|---|---|---|---|---|---|---|---|---|---|---|---|---|---|---|---|---|
|  |  | 515 |  |  |  |  | 520 |  |  |  |  | 525 |  |  |  |  |
| tgg | ggc | gct | atg | cct | gac | gcg | aaa | cgg | tgc | ctc | gat | gcg | gcg | cta | gtg | 1632 |
| Trp | Gly | Ala | Met | Pro | Asp | Ala | Lys | Arg | Cys | Leu | Asp | Ala | Ala | Leu | Val |  |
|  | 530 |  |  |  | 535 |  |  |  |  | 540 |  |  |  |  |  |  |
| acc | ccg | ccg | gaa | gga | cgg | aga | ccg | ggg | aac | ccg | cct | cat | cct | ccc |  | 1680 |
| Thr | Pro | Pro | Glu | Gly | Arg | Arg | Pro | Gly | Asn | Pro | Pro | Ser | His | Pro | Pro |  |
| 545 |  |  |  |  | 550 |  |  |  |  | 555 |  |  |  |  | 560 |  |
| ccc | gag | gct | tca | ccc | ccg | gag | tcg | tct | ccg | ccc | gac | cgg | caa | cat | cct | 1728 |
| Pro | Glu | Ala | Ser | Pro | Pro | Glu | Ser | Ser | Pro | Pro | Asp | Arg | Gln | His | Pro |  |
|  |  |  |  | 565 |  |  |  |  | 570 |  |  |  |  | 575 |  |  |
| cat | cct | cat | cct | cct | cgc | cct | aat | ccc | ccc | gag | gct | tca | cct | ccg | gag | 1776 |
| His | Pro | His | Pro | Pro | Arg | Pro | Asn | Pro | Pro | Glu | Ala | Ser | Pro | Pro | Glu |  |
|  |  |  | 580 |  |  |  |  | 585 |  |  |  |  | 590 |  |  |  |
| ccg | tct | ccg | ccc | aac | tgg | caa | cat | cct | cat | cct | cat | cct | cct | cgc | cct | 1824 |
| Pro | Ser | Pro | Pro | Asn | Trp | Gln | His | Pro | His | Pro | His | Pro | Pro | Arg | Pro |  |
|  |  | 595 |  |  |  |  | 600 |  |  |  |  | 605 |  |  |  |  |
| aat | ccc | ccc | gag | gct | tca | cct | ccg | gag | ccg | tct | ccg | ccc | aac | tgg | caa | 1872 |
| Asn | Pro | Pro | Glu | Ala | Ser | Pro | Pro | Glu | Pro | Ser | Pro | Pro | Asn | Trp | Gln |  |
|  | 610 |  |  |  |  | 615 |  |  |  |  | 620 |  |  |  |  |  |
| cat | cct | cat | cct | cat | cct | cct | cgc | cct | aat | ccc | ccc | ggg | gct | tca | cct | 1920 |
| His | Pro | His | Pro | His | Pro | Pro | Arg | Pro | Asn | Pro | Pro | Gly | Ala | Ser | Pro |  |
| 625 |  |  |  |  | 630 |  |  |  |  | 635 |  |  |  |  | 640 |  |
| ccg | gag | tcg | tct | ccg | ccc | aac | tgg | caa | cat | cct | cat | cct | cat | cct | cct | 1968 |
| Pro | Glu | Ser | Ser | Pro | Pro | Asn | Trp | Gln | His | Pro | His | Pro | His | Pro | Pro |  |
|  |  |  |  | 645 |  |  |  |  | 650 |  |  |  |  | 655 |  |  |
| cgc | cct | aat | ccc | ccc | gag | gct | tca | cct | ccg | cag | tcg | tct | ccg | ccc | gaa | 2016 |
| Arg | Pro | Asn | Pro | Pro | Glu | Ala | Ser | Pro | Pro | Gln | Ser | Ser | Pro | Pro | Glu |  |
|  |  |  | 660 |  |  |  |  | 665 |  |  |  |  | 670 |  |  |  |
| cct | caa | cgt | cct | ttt | tct | cag | tgg | ccc | cac | act | cca | cat | ttt | ttt | cat | 2064 |
| Pro | Gln | Arg | Pro | Phe | Ser | Gln | Trp | Pro | His | Thr | Pro | His | Phe | Phe | His |  |
|  |  | 675 |  |  |  |  | 680 |  |  |  |  | 685 |  |  |  |  |
| tat | cat | ccc | tac | cct | gga | tat | aat | ctt | cct | tat | ttt | act | tac | cat | cag | 2112 |
| Tyr | His | Pro | Tyr | Pro | Gly | Tyr | Asn | Leu | Pro | Tyr | Phe | Thr | Tyr | His | Gln |  |
|  | 690 |  |  |  |  | 695 |  |  |  |  | 700 |  |  |  |  |  |
| tct | cct | ctt | cct | tat | ggt | ccc | tac | gga | agg | gat | cct | tgt | cct | tgt | gct | 2160 |
| Ser | Pro | Leu | Pro | Tyr | Gly | Pro | Tyr | Gly | Arg | Asp | Pro | Cys | Pro | Cys | Ala |  |
| 705 |  |  |  |  | 710 |  |  |  |  | 715 |  |  |  |  | 720 |  |
| tcc | cac | cct | tat | ccc | gcc | gac | gat | tca | cct | ctg | ggg | tcg | tat | gcg | ccc | 2208 |
| Ser | His | Pro | Tyr | Pro | Ala | Asp | Asp | Ser | Pro | Leu | Gly | Ser | Tyr | Ala | Pro |  |
|  |  |  | 725 |  |  |  |  | 730 |  |  |  |  | 735 |  |  |  |
| gat | cca | tca | cct | ccc | cag | tct | tat | ccc | cca | gaa | cct | tca | cca | tcg | aag | 2256 |
| Asp | Pro | Ser | Pro | Pro | Gln | Ser | Tyr | Pro | Pro | Glu | Pro | Ser | Pro | Ser | Lys |  |
|  |  | 740 |  |  |  |  | 745 |  |  |  |  | 750 |  |  |  |  |
| ccg | tct | cca | cca | gag | ggt | tct | tct | ccg | aga | gtc | cct | tcg | cct | cac | cgg | 2304 |
| Pro | Ser | Pro | Pro | Glu | Gly | Ser | Ser | Pro | Arg | Val | Pro | Ser | Pro | His | Arg |  |
|  |  | 755 |  |  |  |  | 760 |  |  |  |  | 765 |  |  |  |  |
| cat | ccc | agc | aga | tca | cgt | ctc | ccc | tct | gct | gtc | gag | cca | tct | cca | cca | 2352 |
| His | Pro | Ser | Arg | Ser | Arg | Leu | Pro | Ser | Ala | Val | Glu | Pro | Ser | Pro | Pro |  |
|  | 770 |  |  |  |  | 775 |  |  |  |  | 780 |  |  |  |  |  |
| ccg | gct | tcc | cca | cag | ccg | tca | cca | cac | ccc | tct | cca | ccg | gac | act | tct | 2400 |
| Pro | Ala | Ser | Pro | Gln | Pro | Ser | Pro | His | Pro | Ser | Pro | Pro | Asp | Thr | Ser |  |
| 785 |  |  |  |  | 790 |  |  |  |  | 795 |  |  |  |  | 800 |  |
| cca | acc | aag | cct | tct | acc | ccc | ccg | cct | tct | cca | tcc | caa | gat | cct | gaa | 2448 |
| Pro | Thr | Lys | Pro | Ser | Thr | Pro | Pro | Pro | Ser | Pro | Ser | Gln | Asp | Pro | Glu |  |
|  |  |  |  | 805 |  |  |  |  | 810 |  |  |  |  | 815 |  |  |
| ggt | cgt | cgg | gaa | cca | tcc | gaa | gag | gat | gat | cat | aaa | tcc | ctg | agt | gac | 2496 |
| Gly | Arg | Arg | Glu | Pro | Ser | Glu | Glu | Asp | Asp | His | Lys | Ser | Leu | Ser | Asp |  |
|  |  | 820 |  |  |  |  | 825 |  |  |  |  | 830 |  |  |  |  |
| aaa | tca | act | tcc | cac | tca | tcg | gaa | ggt | cat | gct | ggg | gcc | acc | ccc | ctc | 2544 |

```
Lys Ser Thr Ser His Ser Ser Glu Gly His Ala Gly Ala Thr Pro Leu
        835                 840                 845 gcc cga gta gga gtt ctc gct gtt ttt tta act gtt gta gga tta att     2592
Ala Arg Val Gly Val Leu Ala Val Phe Leu Thr Val Val Gly Leu Ile
    850                 855                 860 gtg                                                                  2595
Val
865
```

<210> SEQ ID NO 19
<211> LENGTH: 865
<212> TYPE: PRT
<213> ORGANISM: Neospora sp.
<223> OTHER INFORMATION: NC-p65 cDNA

<400> SEQUENCE: 19

```
Met Arg Ala Ser His Ile Leu Leu Ala Cys Ser Val Leu Ile Val Leu
1               5                   10                  15

Leu Cys Met Asp Ala Arg Gly Leu Arg Val Arg Lys Asp Gly Asp Val
            20                  25                  30

Leu Ser Pro Lys Thr Phe Gln Pro Asp Gly Gly Glu Asn Thr Thr Asp
        35                  40                  45

Pro Ser Asp Ile Ile Glu Glu Val Arg Lys Val Glu Lys Gln Val Glu
    50                  55                  60

Ala Glu Ala Ala Glu Ile Ile Lys Ala Arg Glu Glu His Arg Gly Phe
65                  70                  75                  80

Asn Thr Leu Asp Asp Gly Val Ala Pro Glu Thr Glu Gly Gly His Gly
                85                  90                  95

Leu His Ala Ser Glu Thr Thr Pro Val Ala Glu Leu Glu Pro Gln Asp
            100                 105                 110

Pro Asp Arg Ser Leu Lys Tyr Pro Val Arg Leu Leu Ile Val Asp Lys
        115                 120                 125

Pro Ala Gly Asp Glu Glu Glu Thr Arg Pro Ser Phe Val Gln Thr Ala
    130                 135                 140

Leu His Ser Glu Leu Ala Gln Arg Val Val Lys Glu Leu Asn Gly His
145                 150                 155                 160

Val Asp Val Leu Asp Glu Ser Gly Val Val Leu Val Asp Leu Pro Ala
                165                 170                 175

Asn Thr Thr Asp Lys Gln Leu Lys Glu Val Ile Glu Thr Ala Lys Ala
            180                 185                 190

Gln Gly Ala Ile Val Glu Pro Asp His Met Val Ser Ala Val His Thr
        195                 200                 205

Ser Ser Arg Glu Ser Asn Asp Pro Leu Leu His Glu Leu Trp Ala Leu
    210                 215                 220

Asp Pro Leu Asn Met Arg Ala Ala Trp Asp Ile Leu Thr Thr Ala Glu
225                 230                 235                 240

Leu Gly Gly Asp Arg Arg Pro Leu Val Cys Val Val Asp Thr Gly Ile
                245                 250                 255

Asp Tyr Glu His Pro Asp Leu Arg Glu Asn Met Glu Val Asn Gln Val
            260                 265                 270

Glu Leu His Gly Lys Pro Gly Ile Asp Asp Asn Asn Gly Glu Ile
        275                 280                 285

Asp Asp Ile Tyr Gly Ala Asn Met Val Ser Asp Ser Thr Asp Pro Ala
    290                 295                 300

Asp Asp His Ser His Gly Thr His Val Ala Gly Thr Ile Gly Ala Arg
305                 310                 315                 320
```

```
Gly Asp Asn Gly Val Gly Ile Ala Gly Ile Ala Trp Ala Pro Arg Leu
                325                 330                 335
Ile Ala Cys Lys Phe Leu Lys Pro Arg Gly Arg Gly Phe Asp Ser Asp
            340                 345                 350
Ala Leu Arg Cys Ile Asn Tyr Cys Ala Lys Arg Gly Ala Asp Ile Met
            355                 360                 365
Asn His Ser Trp Ser Gly Ser Asp Ala Ser Glu Ala Leu Arg Gln Ala
        370                 375                 380
Ile Glu Gln Thr Ala Gln Gln Gly Ile Ile His Ile Ala Ala Ala Gly
385                 390                 395                 400
Asn Ser Gly Arg Asp Val Asp Val Thr Pro Asn Tyr Pro Ala Ala Leu
                405                 410                 415
Ser Thr Ala Val Glu Gly Leu Ile Thr Val Gly Asn Met Lys Met Glu
                420                 425                 430
Lys Gln Arg Asp Gly Ser Lys His Phe Ser Leu Ala Glu Ser Ser Asn
            435                 440                 445
Tyr Gly Thr Lys Ser Val Gln Ile Ala Leu Pro Gly Thr Asp Ile Tyr
    450                 455                 460
Ser Thr Ile Pro Val Gln Glu Arg Pro Asp Asp Pro Tyr Gly Trp Lys
465                 470                 475                 480
Thr Gly Thr Ser Met Ala Ala Pro Ala Leu Ser Gly Ile Val Ala Leu
                485                 490                 495
Met Leu Ala Ala Asn Pro Gly Leu Ser Ala Thr Gln Ile Arg Ser Ile
            500                 505                 510
Leu Met Gln Ser Val Asn Arg Thr Pro Glu Leu Ser Thr Arg Val Thr
        515                 520                 525
Trp Gly Ala Met Pro Asp Ala Lys Arg Cys Leu Asp Ala Ala Leu Val
    530                 535                 540
Thr Pro Pro Glu Gly Arg Arg Pro Gly Asn Pro Ser His Pro Pro
545                 550                 555                 560
Pro Glu Ala Ser Pro Glu Ser Ser Pro Asp Arg Gln His Pro
                565                 570                 575
His Pro His Pro Pro Arg Pro Asn Pro Pro Glu Ala Ser Pro Pro Glu
            580                 585                 590
Pro Ser Pro Pro Asn Trp Gln His Pro His Pro His Pro Pro Arg Pro
        595                 600                 605
Asn Pro Pro Glu Ala Ser Pro Pro Glu Pro Ser Pro Asn Trp Gln
    610                 615                 620
His Pro His Pro His Pro Pro Arg Pro Asn Pro Pro Gly Ala Ser Pro
625                 630                 635                 640
Pro Glu Ser Ser Pro Pro Asn Trp Gln His Pro His Pro His Pro Pro
                645                 650                 655
Arg Pro Asn Pro Pro Glu Ala Ser Pro Pro Gln Ser Ser Pro Pro Glu
                660                 665                 670
Pro Gln Arg Pro Phe Ser Gln Trp Pro His Thr Pro His Phe Phe His
            675                 680                 685
Tyr His Pro Tyr Pro Gly Tyr Asn Leu Pro Tyr Phe Thr Tyr His Gln
        690                 695                 700
Ser Pro Leu Pro Tyr Gly Pro Tyr Gly Arg Asp Pro Cys Pro Cys Ala
705                 710                 715                 720
Ser His Pro Tyr Pro Ala Asp Asp Ser Pro Leu Gly Ser Tyr Ala Pro
                725                 730                 735
```

```
Asp Pro Ser Pro Pro Gln Ser Tyr Pro Pro Glu Pro Ser Pro Ser Lys
            740                 745                 750

Pro Ser Pro Pro Glu Gly Ser Ser Pro Arg Val Pro Ser Pro His Arg
        755                 760                 765

His Pro Ser Arg Ser Arg Leu Pro Ser Ala Val Glu Pro Ser Pro Pro
    770                 775                 780

Pro Ala Ser Pro Gln Pro Ser Pro His Pro Ser Pro Asp Thr Ser
785                 790                 795                 800

Pro Thr Lys Pro Ser Thr Pro Pro Ser Pro Ser Gln Asp Pro Glu
                805                 810                 815

Gly Arg Arg Glu Pro Ser Glu Glu Asp Asp His Lys Ser Leu Ser Asp
                820                 825                 830

Lys Ser Thr Ser His Ser Ser Glu Gly His Ala Gly Ala Thr Pro Leu
                835                 840                 845

Ala Arg Val Gly Val Leu Ala Val Phe Leu Thr Val Val Gly Leu Ile
            850                 855                 860

Val
865

<210> SEQ ID NO 20
<211> LENGTH: 27
<212> TYPE: DNA
<213> ORGANISM: Artificial Sequence
<220> FEATURE:
<223> OTHER INFORMATION: Description of Artificial Sequence:3'
      gene-specific primer for 5'-RACE

<400> SEQUENCE: 20
gaggcgaagg gactctcgga gaagaac                                            27

<210> SEQ ID NO 21
<211> LENGTH: 26
<212> TYPE: DNA
<213> ORGANISM: Artificial Sequence
<220> FEATURE:
<223> OTHER INFORMATION: Description of Artificial Sequence:5'
      gene-specific primer for 3'-RACE

<400> SEQUENCE: 21
gaaccttcac catcgaagcc gtctcc                                             26

<210> SEQ ID NO 22
<211> LENGTH: 34
<212> TYPE: DNA
<213> ORGANISM: Artificial Sequence
<220> FEATURE:
<223> OTHER INFORMATION: Description of Artificial Sequence:forward
      primer

<400> SEQUENCE: 22
tcagctcgag caacacggtc acgggaacaa tgag                                    34

<210> SEQ ID NO 23
<211> LENGTH: 35
<212> TYPE: DNA
<213> ORGANISM: Artificial Sequence
<220> FEATURE:
<223> OTHER INFORMATION: Description of Artificial Sequence:reverse
      primer

<400> SEQUENCE: 23
tgacgaattc ccagatgtga cggggacatc acyac                                   35
```